(12) United States Patent
Minton et al.

(10) Patent No.: US 11,048,377 B1
(45) Date of Patent: *Jun. 29, 2021

(54) METHODOLOGIES INVOLVING USE OF AVATAR FOR CLINICAL DOCUMENTATION

(71) Applicant: ALLSCRIPTS SOFTWARE, LLC, Chicago, IL (US)

(72) Inventors: William Paul Minton, Goodlettsville, TN (US); Jerry Lynn Goodman, Stovall, NC (US); Michael C. Rapa, Philadelphia, PA (US); Rufus Brandon Harvey, Boyertown, PA (US); Alvin Lee Ashcraft, West Grove, PA (US); Georgian Vicentiu Grigore, West Chester, PA (US); Kasumo Morris, Exton, PA (US); Diane Carolyn Woodall, Oro-Medonte (CA); Murphy Mathews, Burnaby (CA)

(73) Assignee: ALLSCRIPTS SOFTWARE, LLC, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/669,373

(22) Filed: Oct. 30, 2019

Related U.S. Application Data

(63) Continuation of application No. 15/396,450, filed on Dec. 31, 2016, now Pat. No. 10,489,010, which is a continuation of application No. 15/395,849, filed on Dec. 30, 2016, now abandoned, which is a continuation-in-part of application No. 15/362,763, filed on Nov. 28, 2016, now abandoned, which is a (Continued)

(51) Int. Cl.
| | |
|---|---|
| *G06F 3/0481* | (2013.01) |
| *G06F 3/0482* | (2013.01) |
| *G16H 10/20* | (2018.01) |
| *G06F 3/0488* | (2013.01) |
| *G06F 3/0486* | (2013.01) |
| *G06F 3/0484* | (2013.01) |

(52) U.S. Cl.
CPC ........ *G06F 3/04815* (2013.01); *G06F 3/0482* (2013.01); *G06F 3/0486* (2013.01); *G06F 3/04845* (2013.01); *G06F 3/04883* (2013.01); *G16H 10/20* (2018.01)

(58) Field of Classification Search
CPC ......... G06F 3/048; G16H 10/00; G06Q 50/00
See application file for complete search history.

(56) References Cited

U.S. PATENT DOCUMENTS

| | | |
|---|---|---|
| 5,072,383 A | 12/1991 | Brimm et al. |
| 5,077,666 A | 12/1991 | Brimm et al. |

(Continued)

*Primary Examiner* — Jennifer N To
*Assistant Examiner* — Qi Wan
(74) *Attorney, Agent, or Firm* — Loza & Loza, LLP; Peter Zura

(57) ABSTRACT

A method involves presenting an interface which provides the ability to associate photographic images with an anatomical image for use in clinical documentation. A method involves presenting an interface which displays an anatomical image and lists both common conditions for selection by a user and common treatments for the presented or selected conditions. A method involves presenting an interface which displays an anatomical image providing drill down functionality.

17 Claims, 41 Drawing Sheets

Related U.S. Application Data continuation of application No. 15/207,236, filed on Jul. 11, 2016, now abandoned.

(60) Provisional application No. 62/191,353, filed on Jul. 11, 2015.

(56) References Cited

U.S. PATENT DOCUMENTS

| | | | |
|---|---|---|---|
| 5,247,611 A | 9/1993 | Norden-Paul et al. | |
| 5,253,362 A | 10/1993 | Nolan et al. | |
| 5,325,478 A | 6/1994 | Shelton et al. | |
| 5,924,074 A | 7/1999 | Evans | |
| 7,453,472 B2 | 11/2008 | Geode et al. | |
| 7,793,217 B1 | 12/2010 | Kim et al. | |
| 2002/0052763 A1 | 5/2002 | Jung Richardson | |
| 2002/0109734 A1 | 8/2002 | Umezu | |
| 2003/0061072 A1* | 3/2003 | Baker | G06Q 50/24 705/3 |
| 2003/0146942 A1* | 8/2003 | Helgason | G16H 10/20 705/2 |
| 2003/0197744 A1* | 10/2003 | Irvine | G06F 3/038 715/856 |
| 2004/0015778 A1 | 1/2004 | Britton et al. | |
| 2004/0095397 A1 | 5/2004 | Nojima | |
| 2004/0139092 A1 | 7/2004 | Jones, Jr. et al. | |
| 2005/0138631 A1 | 6/2005 | Bellotti | |
| 2005/0182786 A1 | 8/2005 | Suzuki | |
| 2005/0240381 A1 | 10/2005 | Seiler | |
| 2006/0173858 A1 | 8/2006 | Cantlin et al. | |
| 2007/0244910 A1 | 10/2007 | Mital | |
| 2007/0250511 A1 | 10/2007 | Endler | |
| 2009/0144089 A1* | 6/2009 | Heywood | G16H 40/63 705/3 |
| 2009/0222766 A1* | 9/2009 | Chae | G06F 3/04842 715/835 |
| 2010/0039350 A1 | 2/2010 | Wakefield | |
| 2010/0235771 A1 | 9/2010 | Gregg, III | |
| 2010/0316276 A1 | 12/2010 | Torti | |
| 2011/0082710 A1 | 4/2011 | Subash et al. | |
| 2011/0125526 A1 | 5/2011 | Gustafson | |
| 2011/0161854 A1 | 6/2011 | Shukla | |
| 2011/0231205 A1 | 9/2011 | Letts | |
| 2012/0004932 A1* | 1/2012 | Sorkey | G06Q 10/06 705/3 |
| 2012/0166219 A1 | 8/2012 | Mansour | |
| 2012/0210263 A1* | 8/2012 | Perry | G06F 3/0488 715/769 |
| 2013/0073314 A1 | 3/2013 | Mansour | |
| 2014/0029921 A1 | 1/2014 | Warren | |
| 2014/0143232 A1* | 5/2014 | Abe | G06F 16/9038 707/722 |
| 2015/0227708 A1* | 8/2015 | Jung | G06Q 10/06 705/2 |
| 2015/0278483 A1* | 10/2015 | Pruitt | G16H 10/60 705/3 |
| 2016/0283667 A1* | 9/2016 | Rachapalli | H04L 63/10 |

\* cited by examiner

Doe, John A.
Age: 31 | Sex M | MRN 933145526

Medical History

Active Problems
Type II Diabetes Mellitus (250.00) – w/o mention of complication or manifestation; type II, controlled
Managed by – SMITH, John MD | Onset Date – 16-May-2008
Hypertension (401.0) – Essential hypertension; malignant
Seasonal Allergic Reaction (477.0) – Allergic rhinitis, due to pollen

Current Medications
Accuretic 25-20 mg Oral Tablet; 1 PO QD
Metformin 1000 mg; 1 PO BID
Lantus 20 Units; qH S

Allergies
Cephalosporins
Eggs

Immunizations
Tetanous

Family History

Social History

*FIG. 1*

Doe, John A.
Age: 31 | Sex M | MRN 933145526

Medical History

Active Problems
Type II Diabetes Mellitus (250.00) – w/o mention of complication or manifestation; type II, controlled
Managed by – SMITH, John MD | Onset Date – 16-May-2008
Hypertension (401.0) – Essential hypertension; malignant
Seasonal Allergic Reaction (477.0) – Allergic rhinitis, due to pollen

Current Medications
Accuretic 25-20 mg Oral Tablet; 1 PO QD
Metformin 1000 mg; 1 PO BID
Lantus 20 Units; qH S

Allergies
Cephalosporins
Eggs

Immunizations
Tetanous

Family History

Social History

*FIG. 9*

Doe, John A.
Age: 31 | Sex M | MRN 933145526

Medical History

Active Problems
Type II Diabetes Mellitus (250.00) – w/o mention of complication or manifestation; type II, controlled
Managed by – SMITH, John MD | Onset Date – 16-May-2008
Hypertension (401.0) – Essential hypertension; malignant
Seasonal Allergic Reaction (477.0) – Allergic rhinitis, due to pollen

Current Medications
Accuretic 25-20 mg Oral Tablet; 1 PO QD
Metformin 1000 mg; 1 PO BID
Lantus 20 Units; qH S

Allergies
Cephalosporins
Eggs

Immunizations
Tetanous

Family History

Social History

*FIG. 10*

Doe, John A.
Age: 31 | Sex M | MRN 933145526

Medical History

Active Problems
Type II Diabetes Mellitus (250.00) – w/o mention of complication or manifestation; type II, controlled
Managed by – SMITH, John MD | Onset Date – 16-May-2008
Hypertension (401.0) – Essential hypertension; malignant
Seasonal Allergic Reaction (477.0) – Allergic rhinitis, due to pollen

Current Medications
Accuretic 25-20 mg Oral Tablet; 1 PO QD
Metformin 1000 mg; 1 PO BID
Lantus 20 Units; qH S

Allergies
Cephalosporins
Eggs

Immunizations
Tetanous

Family History

Social History

Doe, John A.
Age: 31 | Sex M | MRN 933145526

Medical History

Active Problems
Type II Diabetes Mellitus (250.00) – w/o mention of complication or manifestation; type II, controlled
Managed by – SMITH, John MD | Onset Date – 16-May-2008
Hypertension (401.0) – Essential hypertension; malignant
Seasonal Allergic Reaction (477.0) – Allergic rhinitis, due to pollen

Current Medications
Accuretic 25-20 mg Oral Tablet; 1 PO QD
Metformin 1000 mg; 1 PO BID
Lantus 20 Units; qH S

Allergies
Cephalosporins
Eggs

Immunizations
Tetanous

Family History

Social History

Doe, John A.
Age: 31 | Sex M | MRN 933145526

Medical History

Active Problems
Type II Diabetes Mellitus (250.00) – w/o mention of complication or manifestation; type II, controlled
Managed by – SMITH, John MD | Onset Date – 16-May-2008
Hypertension (401.0) – Essential hypertension; malignant
Seasonal Allergic Reaction (477.0) – Allergic rhinitis, due to pollen

Current Medications
Accuretic 25-20 mg Oral Tablet; 1 PO QD
Metformin 1000 mg; 1 PO BID
Lantus 20 Units; qH S

Allergies
Cephalosporins
Eggs

Immunizations
Tetanous

Family History

Social History

Doe, John A.
Age: 31 | Sex M | MRN 933145526

Medical History

Active Problems
Type II Diabetes Mellitus (250.00) – w/o mention of complication or manifestation; type II, controlled
Managed by – SMITH, John MD | Onset Date – 16-May-2008
Hypertension (401.0) – Essential hypertension; malignant
Seasonal Allergic Reaction (477.0) – Allergic rhinitis, due to pollen

Current Medications
Accuretic 25-20 mg Oral Tablet; 1 PO QD
Metformin 1000 mg; 1 PO BID
Lantus 20 Units; qH S

Allergies
Cephalosporins
Eggs

Immunizations
Tetanous

Family History

Social History

Search

FIG. 35

METHODOLOGIES INVOLVING USE OF AVATAR FOR CLINICAL DOCUMENTATION

CROSS-REFERENCE TO RELATED APPLICATION

The present application is a U.S. continuation of, and claims priority under 35 U.S.C. § 120 to, U.S. Pat. No. 10,489,010, which claims priority under 35 U.S.C. § 120 to U.S. patent application Ser. No. 15/395,849, filed Dec. 30, 2016, which is a U.S. continuation-in-part patent application of, and claims priority under 35 U.S.C. § 120 to, U.S. patent application Ser. No. 15/362,763, filed Nov. 28, 2016, and which '763 application is a U.S. continuation of, and claims priority under 35 U.S.C. § 120 to, U.S. patent application Ser. No. 15/207,236, filed Jul. 11, 2016, which '236 application is a U.S. nonprovisional patent application of, and claims priority under 35 U.S.C. § 119(e) to, U.S. provisional patent application 62/191,353, filed Jul. 11, 2015, each of which are incorporated herein by reference in their entirety. The present application also incorporates herein by reference the disclosure of each of Exhibits 1 to 4 of the appendix of the '849 application.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to clinical documentation in a medical context. A need exists for improvement in clinical documentation. This need and other needs are addressed by one or more aspects of the present invention.

SUMMARY OF THE INVENTION

The present invention includes many aspects and features. Moreover, while many aspects and features relate to, and are described in a particular context, the present invention is not limited to use only in this context, as will become apparent from the following summaries and detailed descriptions of aspects, features, and one or more embodiments of the present invention.

Accordingly, one aspect of the present invention relates to presenting an interface which provides the ability to associate photographic images with an anatomical image for use in clinical documentation.

Another aspect relates to presenting an interface which displays an anatomical image and lists both common conditions for selection by a user and common treatments for the presented or selected conditions.

Another aspect relates to presenting an interface which displays an anatomical image providing drill down functionality.

Another aspect relates to a method related to graphical user interfaces for a healthcare software application. The method includes displaying, to a user via an electronic display associated with an electronic device, a first interface of the healthcare software application, the first interface including a three dimensional image representing an avatar for a patient; receiving, from the user via one or more input devices associated with the electronic device, user input corresponding to interaction with a first portion of the avatar, the first portion of the avatar being associated with a first hotspot of the avatar; displaying, to the user via the electronic display, a second interface of the healthcare software application, the second interface being configured to allow the user to add a photo for association with the first hotspot of the avatar; receiving, from the user via one or more input devices associated with the electronic device, user input corresponding to selection of one or more photos for association with the first hotspot of the avatar; and displaying, to the user via the electronic display, the first interface updated to include a numerical indication of the number of photos associated with the first hotspot of the avatar.

In a feature of this aspect, the method further comprises receiving, from the user via one or more input devices associated with the electronic device, user input corresponding to an indication to edit one of the one or more photos for association with the first hotspot of the avatar. In one or more preferred implementations in accordance with this feature, the method further comprises displaying an interface of the healthcare software application configured to allow a user to edit a photo. In one or more preferred implementations in accordance with this feature, the method further comprises opening a graphics editor configured to allow a user to edit a photo.

In a feature of this aspect, the first hotspot comprises a user's arm.

In a feature of this aspect, the first hotspot comprises a user's hand.

In a feature of this aspect, the user input corresponding to interaction with a first portion of the avatar comprises clicking on the first portion of the avatar.

In a feature of this aspect, the electronic device comprises a touchscreen device, and receiving user input corresponding to interaction with a first portion of the avatar comprises receiving, via the touchscreen, one or more taps.

In a feature of this aspect, the method further comprises receiving user input corresponding to interaction with a second portion of the avatar, and displaying an enlarged view of the second portion of the avatar in response thereto. In one or more preferred implementations in accordance with this feature, the user input corresponding to interaction with a second portion of the avatar comprises hovering over the second portion of the avatar. In one or more preferred implementations in accordance with this feature, the user input corresponding to interaction with a second portion of the avatar comprises double clicking on the second portion of the avatar. In one or more preferred implementations in accordance with this feature, the user input corresponding to interaction with a second portion of the avatar comprises double tapping on the second portion of the avatar. In one or more preferred implementations in accordance with this feature, the user input corresponding to interaction with a second portion of the avatar comprises pressing and holding on the second portion of the avatar.

In a feature of this aspect, the method further comprises receiving user input corresponding to interaction with a second portion of the avatar, and displaying an enhanced view of the second portion of the avatar in response thereto.

In a feature of this aspect, the electronic device comprises a desktop or laptop computer.

In a feature of this aspect, the electronic device comprises an all in one computer.

In a feature of this aspect, the electronic device comprises a tablet.

In a feature of this aspect, the electronic device comprises a phone.

In a feature of this aspect, the electronic device comprises a mobile device.

Another aspect relates to a method related to a graphical user interface for a healthcare software application. The method includes displaying, to a user via an electronic display associated with an electronic device, a first interface of the healthcare software application, the first interface including a three dimensional image representing an avatar for a patient, the avatar comprising a plurality of hotpots, a first listing of a plurality of problems that can be associated with the avatar of the patient for clinical documentation, and a second listing of a plurality of interventions that can be associated with the avatar of the patient for clinical documentation. The method further includes receiving, from the user via one or more input devices associated with the electronic device, user input corresponding to dragging of a first listed problem item of the plurality of problems over a first hotspot of the plurality of hotspots; in response to the first problem item being dragged over the first hotspot, highlighting, to visually indicate association is possible, the first hotspot; receiving, from the user via one or more input devices associated with the electronic device, user input corresponding to dropping of the dragged first problem item on the first hotspot; in response to the dropping of the dragged first problem item on the first hotspot, displaying the first problem item adjacent the avatar and visually indicating the association of the first problem item with the first hotspot; receiving, from the user via one or more input devices associated with the electronic device, user input corresponding to dragging of a first listed intervention item of the plurality of interventions over a second hotspot of the plurality of hotspots; in response to the first intervention item being dragged over the second hotspot, highlighting, to visually indicate association is possible, the second hotspot; receiving, from the user via one or more input devices associated with the electronic device, user input corresponding to dropping of the dragged first intervention item on the second hotspot; in response to the dropping of the dragged first intervention item on the second hotspot, displaying the first intervention item adjacent the avatar and visually indicating the association of the first intervention item with the second hotspot; receiving, from the user via one or more input devices associated with the electronic device, user input corresponding to dragging of a second listed intervention item of the plurality of interventions over the first problem item displayed adjacent the avatar; in response to the second intervention item being dragged over the first problem item, highlighting, to visually indicate association is possible, the first problem item displayed adjacent the avatar; receiving, from the user via one or more input devices associated with the electronic device, user input corresponding to dropping of the dragged second intervention item on the first problem item displayed adjacent the avatar; in response to the dropping of the dragged second intervention item on the first problem item, displaying the second intervention item adjacent the first problem item and visually indicating the association of the second intervention item with the first problem item; receiving, from the user via one or more input devices associated with the electronic device, user input corresponding to dragging of a third listed intervention item of the plurality of interventions over the second intervention item displayed adjacent the first problem item; in response to the third intervention item being dragged over the second intervention item, highlighting, to visually indicate association is possible, the second intervention item displayed adjacent the first problem item; receiving, from the user via one or more input devices associated with the electronic device, user input corresponding to dropping of the dragged third intervention item on the second intervention item displayed adjacent the first problem item; and in response to the dropping of the dragged third intervention item on the second intervention item, displaying the third intervention item adjacent the second intervention item and visually indicating the association of the third intervention item with the second intervention item.

In a feature of this aspect, the method further comprises receiving, from the user via one or more input devices associated with the electronic device, user input corresponding to dragging of a second listed problem item of the plurality of problems over the first hotspot of the plurality of hotspots; in response to the second problem item being dragged over the first hotspot, highlighting, to visually indicate association is possible, the first hotspot; receiving, from the user via one or more input devices associated with the electronic device, user input corresponding to dropping of the dragged second problem item on the first hotspot; and in response to the dropping of the dragged second problem item on the first hotspot, displaying the second problem item adjacent the avatar and visually indicating the association of the second problem item with the first hotspot.

In a feature of this aspect, the method further comprises receiving, from the user via one or more input devices associated with the electronic device, user input corresponding to dragging of a second listed problem item of the plurality of problems over the second hotspot of the plurality of hotspots; in response to the second problem item being dragged over the second hotspot, highlighting, to visually indicate association is possible, the second hotspot; receiving, from the user via one or more input devices associated with the electronic device, user input corresponding to dropping of the dragged second problem item on the second hotspot; and in response to the dropping of the dragged second problem item on the second hotspot, displaying the second problem item adjacent the avatar and visually indicating the association of the second problem item with the second hotspot.

In a feature of this aspect, the method further comprises receiving, from the user via one or more input devices associated with the electronic device, user input corresponding to dragging of a second listed problem item of the plurality of problems over a third hotspot of the plurality of hotspots; in response to the second problem item being dragged over the third hotspot, highlighting, to visually indicate association is possible, the third hotspot; receiving, from the user via one or more input devices associated with the electronic device, user input corresponding to dropping of the dragged second problem item on the third hotspot; and in response to the dropping of the dragged second problem item on the third hotspot, displaying the second problem item adjacent the avatar and visually indicating the association of the second problem item with the third hotspot.

In a feature of this aspect, the method further comprises receiving, from the user via one or more input devices associated with the electronic device, user input corresponding to dragging of a fourth listed intervention item of the plurality of interventions over the second hotspot of the plurality of hotspots; in response to the fourth intervention item being dragged over the second hotspot, highlighting, to visually indicate association is possible, the second hotspot; receiving, from the user via one or more input devices associated with the electronic device, user input corresponding to dropping of the dragged fourth intervention item on the second hotspot; and in response to the dropping of the dragged fourth intervention item on the second hotspot, displaying the fourth intervention item adjacent the avatar and visually indicating the association of the fourth intervention item with the second hotspot.

In a feature of this aspect, the method further comprises receiving, from the user via one or more input devices associated with the electronic device, user input corresponding to dragging of a fourth listed intervention item of the plurality of interventions over the first hotspot of the plurality of hotspots; in response to the fourth intervention item being dragged over the first hotspot, highlighting, to visually indicate association is possible, the first hotspot; receiving, from the user via one or more input devices associated with the electronic device, user input corresponding to dropping of the dragged fourth intervention item on the first hotspot; and in response to the dropping of the dragged fourth intervention item on the first hotspot, displaying the fourth intervention item adjacent the avatar and visually indicating the association of the fourth intervention item with the first hotspot.

In a feature of this aspect, the method further comprises receiving, from the user via one or more input devices associated with the electronic device, user input corresponding to dragging of a second listed problem item of the plurality of problems over a portion of the avatar; and in response to the second problem item being dragged over the portion of the avatar, displaying an enlarged view of the portion of the avatar.

In a feature of this aspect, the method further comprises receiving, from the user via one or more input devices associated with the electronic device, user input corresponding to dragging of a second listed problem item of the plurality of problems over a portion of the avatar; and in response to the second problem item being dragged over the portion of the avatar, displaying an enhanced view of the portion of the avatar.

In a feature of this aspect, the method further comprises receiving, from the user via one or more input devices associated with the electronic device, user input corresponding to dragging of a second listed problem item of the plurality of problems over a portion of the avatar; in response to the second problem item being dragged over the portion of the avatar, displaying an enlarged view of the portion of the avatar; receiving, from the user via one or more input devices associated with the electronic device, user input corresponding to further dragging of the second problem item over a third hotspot in the enlarged view; in response to the second problem item being dragged over the third hotspot, highlighting, to visually indicate association is possible, the third hotspot; receiving, from the user via one or more input devices associated with the electronic device, user input corresponding to dropping of the dragged second problem item on the third hotspot; and in response to the dropping of the dragged second problem item on the third hotspot, displaying the second problem item adjacent the avatar and visually indicating the association of the second problem item with the third hotspot.

In a feature of this aspect, the method further comprises receiving, from the user via one or more input devices associated with the electronic device, user input corresponding to dragging of a second listed problem item of the plurality of problems over a portion of the avatar; in response to the second problem item being dragged over the portion of the avatar, displaying an enlarged view of the portion of the avatar; receiving, from the user via one or more input devices associated with the electronic device, user input corresponding to further dragging of the second problem item over a third hotspot in the enlarged view; in response to the second problem item being dragged over the third hotspot, highlighting, to visually indicate association is possible, the third hotspot; receiving, from the user via one or more input devices associated with the electronic device, user input corresponding to dropping of the dragged second problem item on the third hotspot; and in response to the dropping of the dragged second problem item on the third hotspot, displaying the second problem item adjacent the avatar and visually indicating the association of the second problem item with the portion.

In a feature of this aspect, the method further comprises receiving, from the user via one or more input devices associated with the electronic device, user input corresponding to dragging of a second listed problem item of the plurality of problems over a portion of the avatar; in response to the second problem item being dragged over the portion of the avatar, displaying an enhanced view of the portion of the avatar; receiving, from the user via one or more input devices associated with the electronic device, user input corresponding to further dragging of the second problem item over a third hotspot in the enhanced view; in response to the second problem item being dragged over the third hotspot, highlighting, to visually indicate association is possible, the third hotspot; receiving, from the user via one or more input devices associated with the electronic device, user input corresponding to dropping of the dragged second problem item on the third hotspot; and in response to the dropping of the dragged second problem item on the third hotspot, displaying the second problem item adjacent the avatar and visually indicating the association of the second problem item with the third hotspot.

In a feature of this aspect, the method further comprises receiving, from the user via one or more input devices associated with the electronic device, user input corresponding to dragging of a second listed problem item of the plurality of problems over a portion of the avatar; in response to the second problem item being dragged over the portion of the avatar, displaying an enhanced view of the portion of the avatar; receiving, from the user via one or more input devices associated with the electronic device, user input corresponding to further dragging of the second problem item over a third hotspot in the enhanced view; in response to the second problem item being dragged over the third hotspot, highlighting, to visually indicate association is possible, the third hotspot; receiving, from the user via one or more input devices associated with the electronic device, user input corresponding to dropping of the dragged second problem item on the third hotspot; and in response to the dropping of the dragged second problem item on the third hotspot, displaying the second problem item adjacent the avatar and visually indicating the association of the second problem item with the portion.

In a feature of this aspect, the electronic device comprises a desktop or laptop computer.

In a feature of this aspect, the electronic device comprises an all in one computer.

In a feature of this aspect, the electronic device comprises a tablet.

In a feature of this aspect, the electronic device comprises a phone.

In a feature of this aspect, the electronic device comprises a mobile device.

In a feature of this aspect, the electronic device comprises a touchscreen device and receiving, from the user via one or more input devices associated with the electronic device, user input corresponding to dragging of a first listed problem item comprises receiving user input via a touchscreen.

Another aspect relates to a method related to a graphical user interface for a healthcare software application. The method includes displaying, to a user via an electronic display associated with an electronic device, a first interface of the healthcare software application, the first interface including a three dimensional image representing an avatar for a patient, the avatar comprising a plurality of hotpots, a first listing of a plurality of problems that can be associated with the avatar of the patient for clinical documentation, and a second listing of a plurality of interventions that can be associated with the avatar of the patient for clinical documentation. The method further includes receiving, from the user via one or more input devices associated with the electronic device, user input corresponding to dragging of a first listed problem item of the plurality of problems over a first hotspot of the plurality of hotspots; in response to the first problem item being dragged over the first hotspot, highlighting, to visually indicate association is possible, the first hotspot; receiving, from the user via one or more input devices associated with the electronic device, user input corresponding to dropping of the dragged first problem item on the first hotspot; in response to the dropping of the dragged first problem item on the first hotspot, displaying the first problem item adjacent the avatar and visually indicating the association of the first problem item with the first hotspot; receiving, from the user via one or more input devices associated with the electronic device, user input corresponding to dragging of a first listed intervention item of the plurality of interventions over the first problem item displayed adjacent the avatar; in response to the first intervention item being dragged over the first problem item, highlighting, to visually indicate association is possible, the first problem item displayed adjacent the avatar; receiving, from the user via one or more input devices associated with the electronic device, user input corresponding to dropping of the dragged first intervention item on the first problem item displayed adjacent the avatar; in response to the dropping of the dragged first intervention item on the first problem item, displaying the first intervention item adjacent the first problem item and visually indicating the association of the first intervention item with the first problem item; receiving, from the user via one or more input devices associated with the electronic device, user input corresponding to dragging of a second listed intervention item of the plurality of interventions over the first intervention item displayed adjacent the first problem item; in response to the second intervention item being dragged over the first intervention item, highlighting, to visually indicate association is possible, the first intervention item displayed adjacent the first problem item; receiving, from the user via one or more input devices associated with the electronic device, user input corresponding to dropping of the dragged second intervention item on the first intervention item displayed adjacent the first problem item; and in response to the dropping of the dragged second intervention item on the first intervention item, displaying the second intervention item adjacent the first intervention item and visually indicating the association of the second intervention item with the first intervention item.

Another aspect relates to one or more computer readable media containing computer-executable instructions for performing a disclosed method.

Another aspect relates to software for performing a disclosed method.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings.

FIG. 1 illustrates an exemplary interface of an electronic healthcare records application in accordance with one or more preferred implementations which includes an avatar.

FIG. 9 illustrates display of an indication of a number of photos or images associated with a portion of an avatar.

FIGS. 10-18 illustrate exemplary functionality related to an avatar.

FIG. 19 illustrates an exemplary interface in accordance with one or more preferred implementations which includes an avatar and a listing of problems and interventions that can be dragged onto an avatar for the purpose of clinical documentation for a patient.

FIGS. 20-22 illustrate dragging of a firearms problem item onto an arm hotspot of an avatar.

FIGS. 27-41 illustrate exemplary functionality related to an avatar.

DETAILED DESCRIPTION

Figure 2:
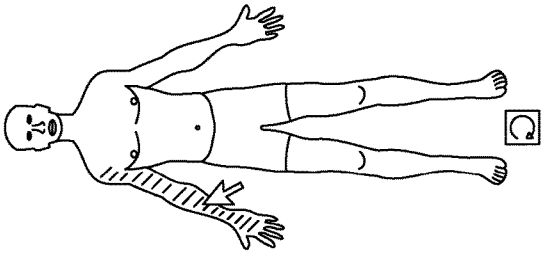
FIG. 2 illustrates highlighting of a portion of an avatar.

As a preliminary matter, it will readily be understood by one having ordinary skill in the relevant art ("Ordinary Artisan") that the invention has broad utility and application. Furthermore, any embodiment discussed and identified as being "preferred" is considered to be part of a best mode contemplated for carrying out the invention. Other embodiments also may be discussed for additional illustrative purposes in providing a full and enabling disclosure of the invention. Furthermore, an embodiment of the invention may incorporate only one or a plurality of the aspects of the invention disclosed herein; only one or a plurality of the features disclosed herein; or combination thereof. As such, many embodiments are implicitly disclosed herein and fall within the scope of what is regarded as the invention.

Accordingly, while the invention is described herein in detail in relation to one or more embodiments, it is to be understood that this disclosure is illustrative and exemplary of the invention, and is made merely for the purposes of providing a full and enabling disclosure of the invention. The detailed disclosure herein of one or more embodiments is not intended, nor is to be construed, to limit the scope of patent protection afforded the invention in any claim of a patent issuing here from, which scope is to be defined by the claims and the equivalents thereof. It is not intended that the scope of patent protection afforded the invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the invention. Accordingly, it is intended that the scope of patent protection afforded the invention is to be defined by the issued claim(s) rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. 112, paragraph 6 or subsection (f), no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." When used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the invention are next described. The following description of one or more preferred embodiments is merely exemplary in nature and is in no way intended to limit the invention, its implementations, or uses.

In accordance with one or more preferred implementations, software provides the ability to associate photographic images with an anatomical image for use in clinical documentation. A photograph can be selected for association with any designated "hot spot" on the anatomical image (e.g. the anterior view of the hand). Preferably, the number of images associated with each hot spot is shown on the anatomical image. Preferably, when a hot spot is selected, a gallery view of the associated images is displayed.

In one or more preferred implementations, an anatomical image comprising a three dimensional full body avatar is utilized. Preferably, an interface allows the avatar to be rotated or turned so that both anterior and posterior views of the avatar are available in the same space, conserving screen real estate.

Preferably, an avatar is based on the gender (e.g. male/female), age (e.g. child/adult), and/or ethnicity of the patient for whom clinical documentation is occurring. Preferably the use of a lifelike image associated to patient attributes assists the user in ensuring the correct patient is being documented on.

One or more preferred implementations provide for conservation of screen space (e.g. versus two images, one back/one front), quick association of photographs with specific anatomical regions, quick index view of how many photographs are associated with any particular hot spot, available annotation of each image via a simple graphics program such as Microsoft Paint. In accordance with one or more preferred implementations, images are available via hyperlink on a patient chart display.

FIG. 1 illustrates an exemplary interface in accordance with one or more preferred implementations. This specific interface represents an interface for an electronic healthcare records application, although it will be appreciated that a similar interface may be utilized for other applications, such as a web app or a mobile app.

The interface includes an anatomical image comprising a full body avatar. In accordance with one or more preferred implementations, a user may interact with (e.g. hover a mouse pointer over or touch via a touchscreen) a portion of the avatar (e.g. a hotspot) to effect highlighting of that portion, as illustrated in FIG. 2. In accordance with one or more preferred implementations, a user may interact with a portion of the avatar (e.g. click on a hotspot of the image or even just a point on the image) to access a photo manager interface which will allow the user to upload one or more photos for association with that portion of the image.

Figure 3:
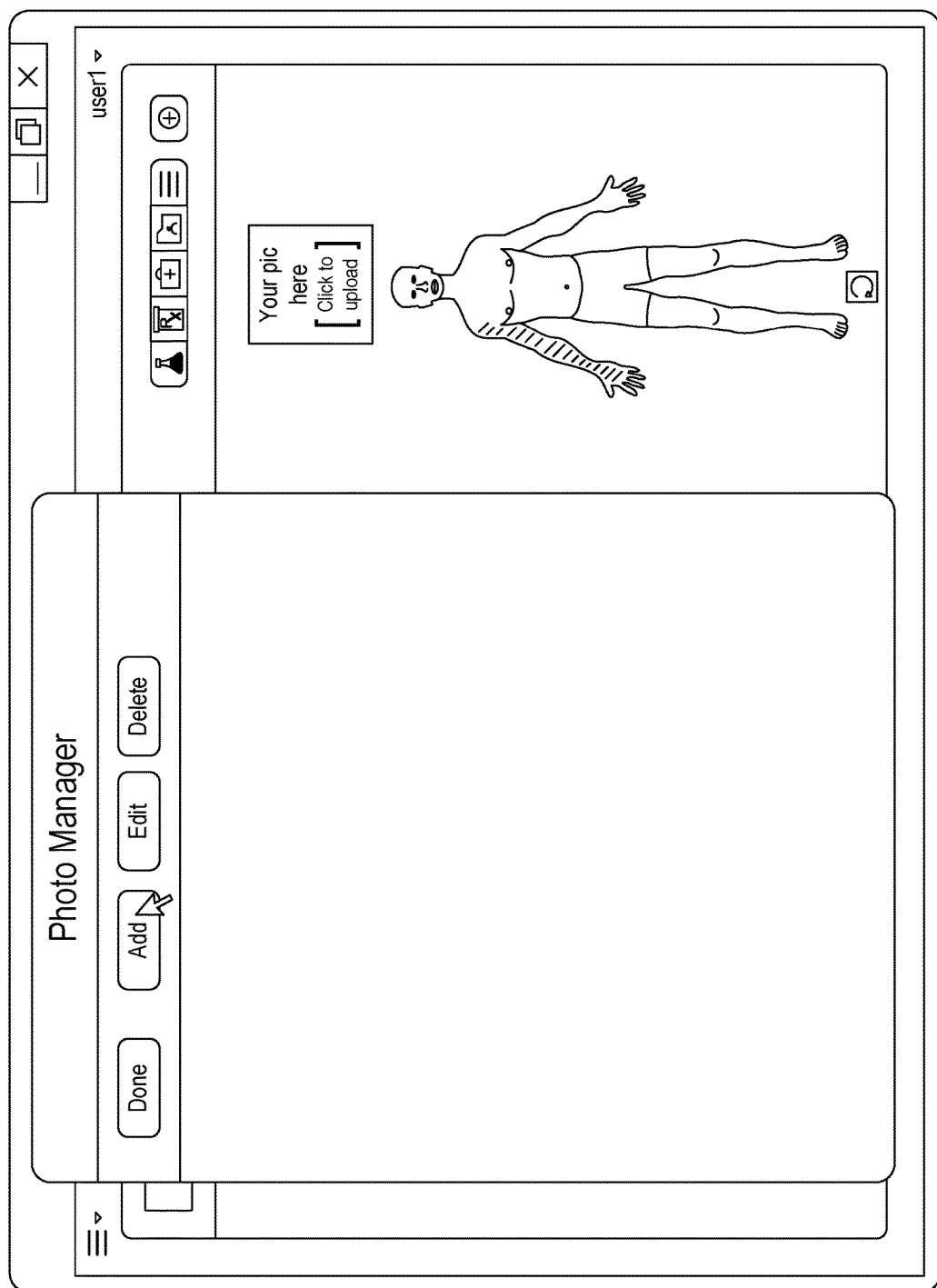
FIG. 3-4 illustrate an exemplary photo manager interface which is configured to allow a user to add photos in association with a previously selected portion of an avatar.
Figure 4:
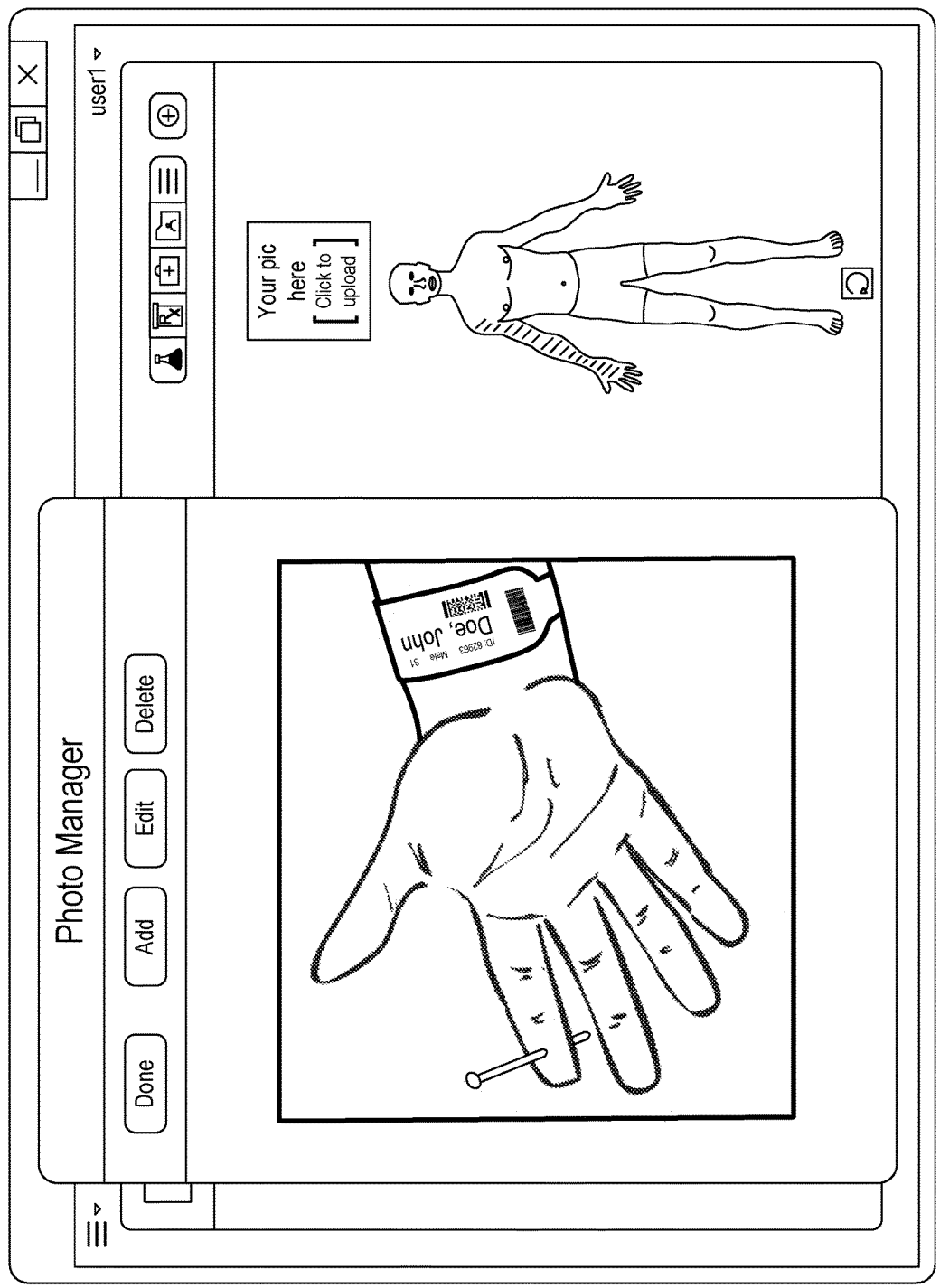

FIG. 3 illustrates an exemplary photo manager interface which is configured to allow a user to add photos in association with the previously selected portion of the avatar. A user can interact with the "Add" button to access a file dialog which will allow the user to select a saved image. Once the user selects a saved image, it will be displayed in the photo manager, as illustrated in FIG. 4.

Figure 5:
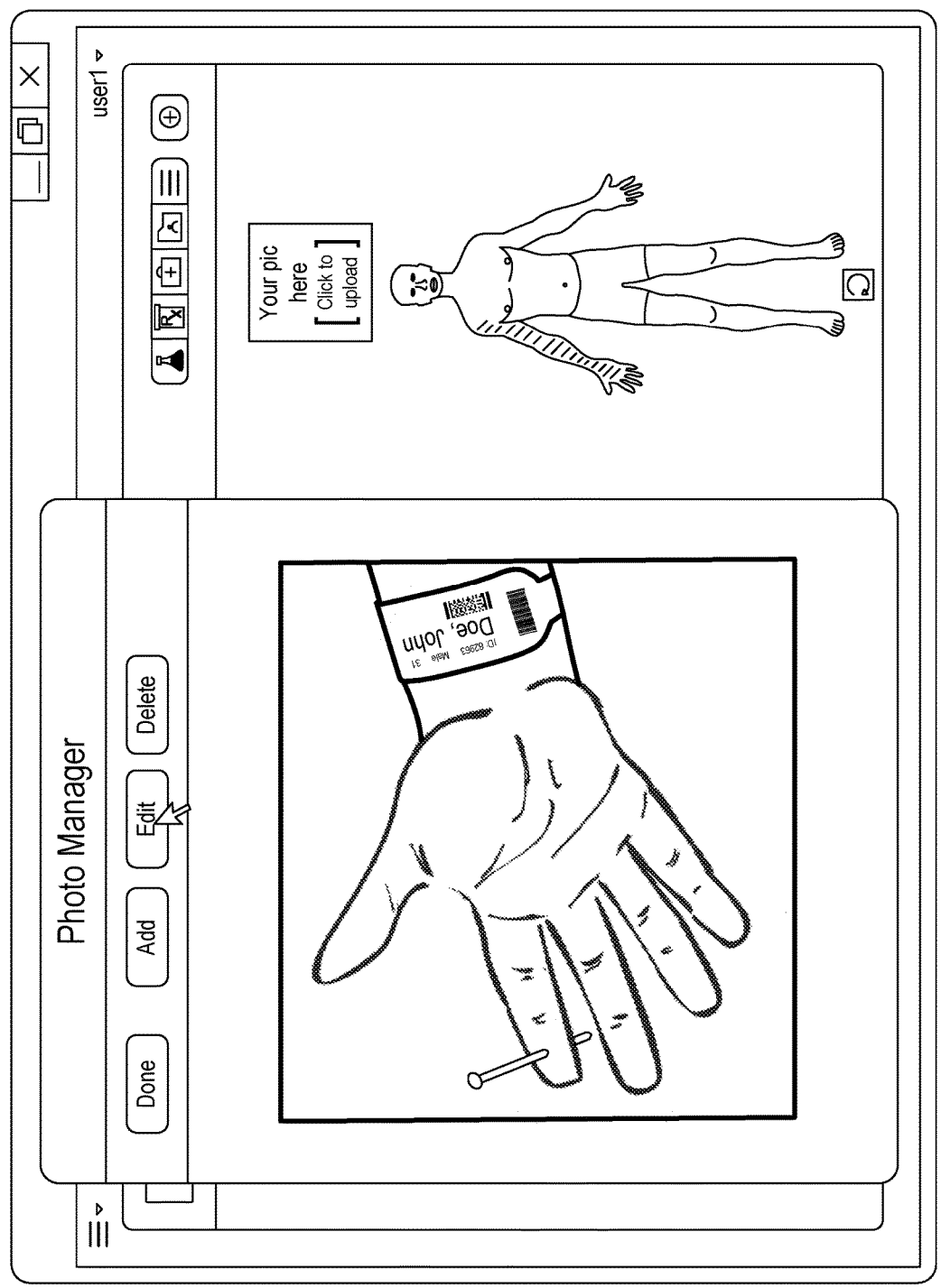
FIG. 5-8 illustrate editing of a photo for association with a previously selected portion of an avatar.
Figure 6:
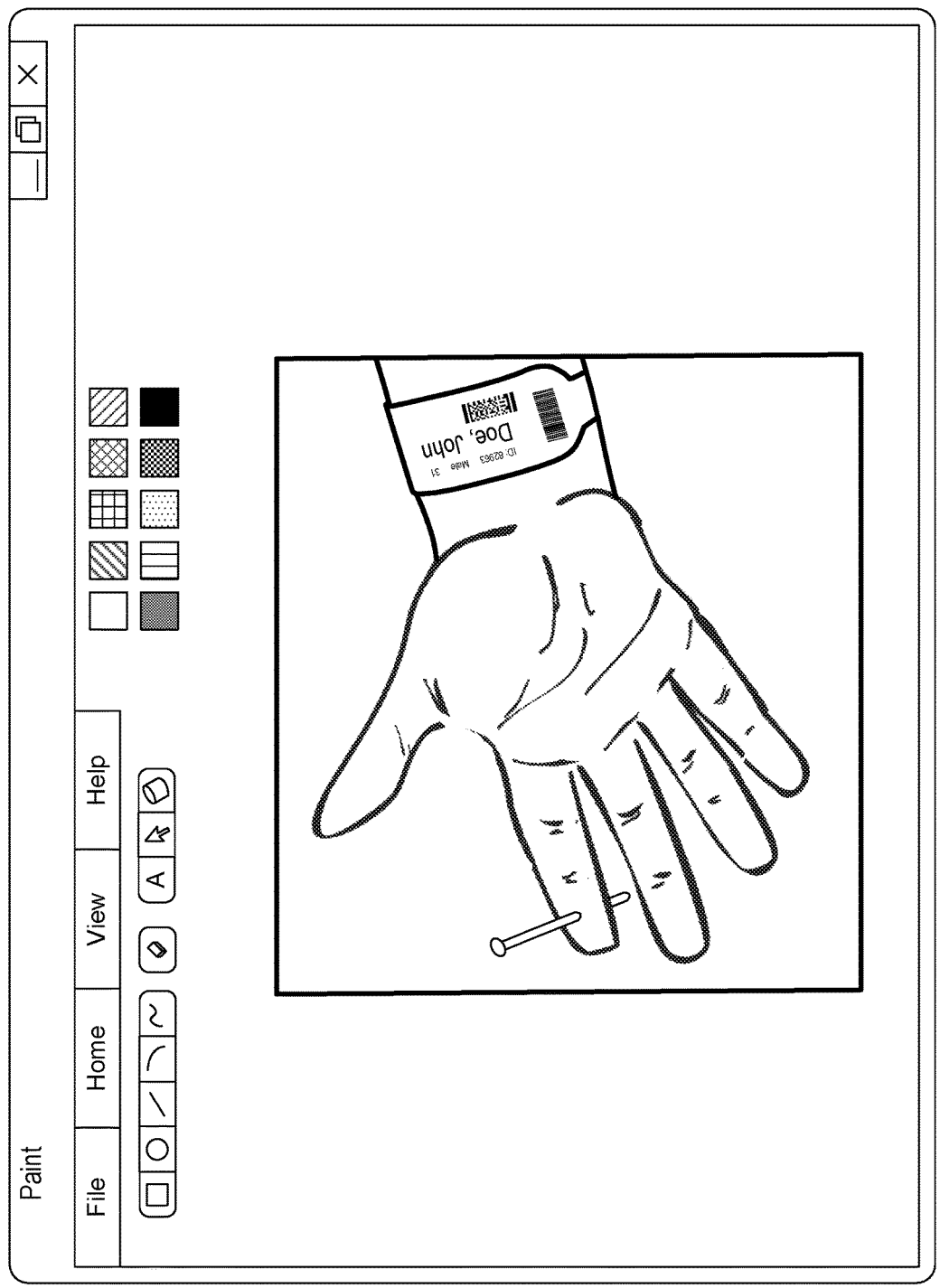
Figure 7:
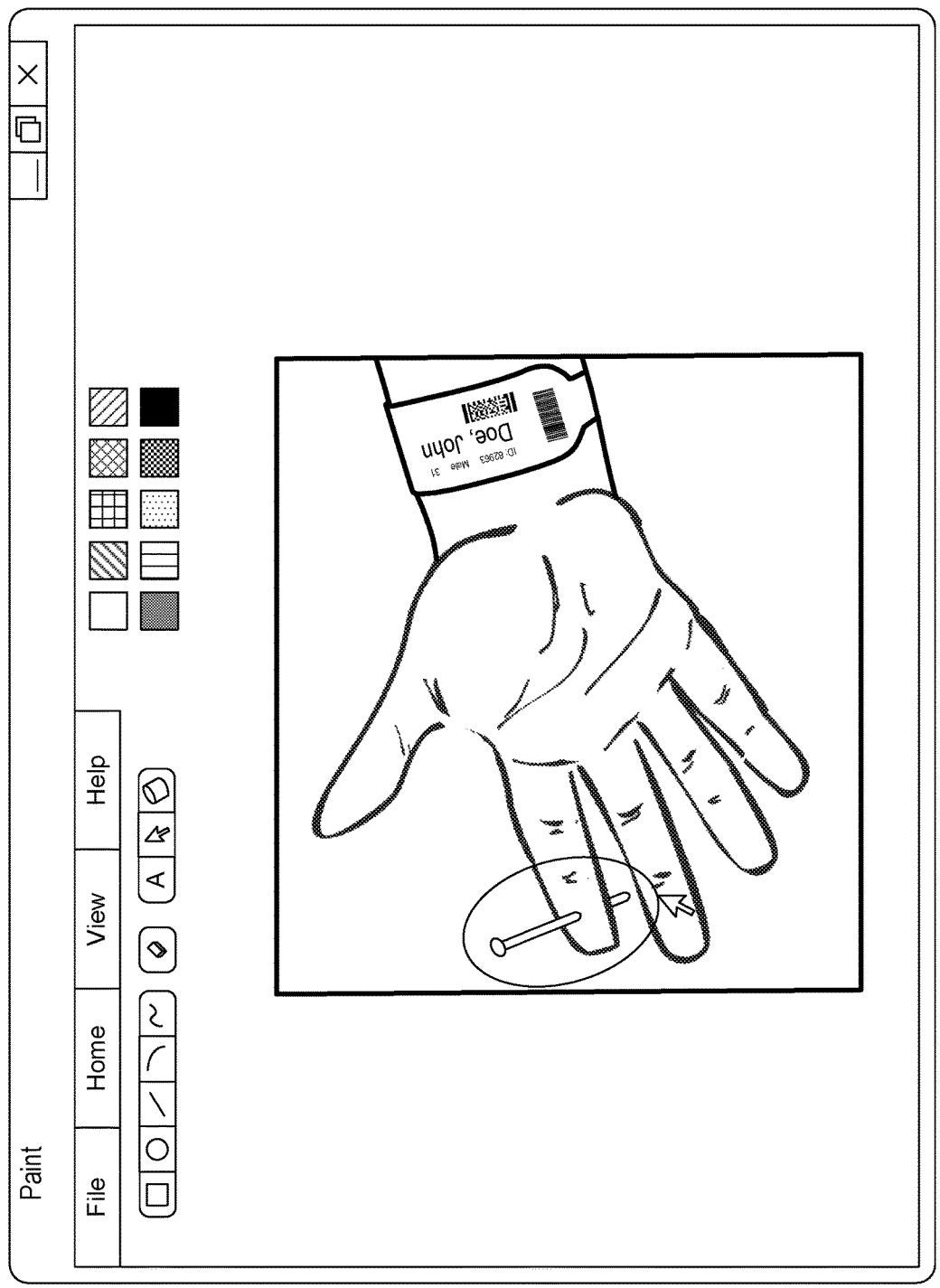
Figure 8:
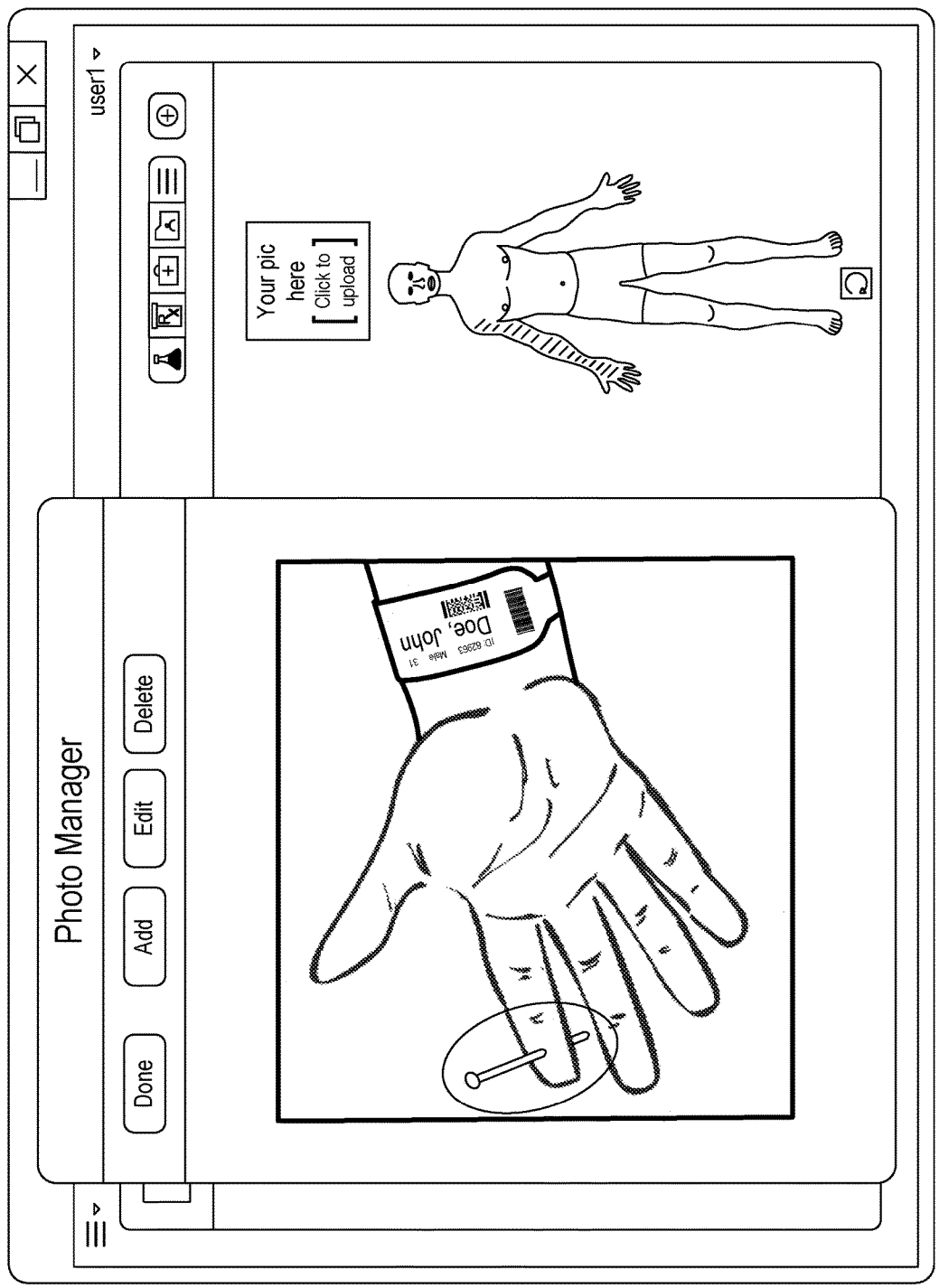

In accordance with one or more preferred implementations, a photo manager interface is configured to allow a user to edit images. In accordance with one or more preferred implementations, photo editing is performed natively (e.g. within an electronic healthcare records application), while in accordance with one or more preferred implementations, photo editing is performed in another application, such as a paint application or other graphics editor. FIGS. 5-6 illustrate user interaction with an edit interface element to effect editing of a photo. A user can utilize editing tools to, inter alia, annotate a photo, as illustrated in FIG. 7. The edited photo can be saved in the photo manager, as illustrated in FIG. 8.

Once a user has selected one or more photos for association with a selected portion of an avatar, the user can indicate that he is done, and once again view an interface including the avatar, this time updated to indicate that a photo or image is associated with the previously selected portion of the avatar, as illustrated in FIG. 9. In FIG. 9, the numeral "1" inside of a box indicates that one photo or image is associated with the patient's arm.

It will be appreciated that various levels of granularity with respect to body portions may be utilized. For example, although FIG. 2 illustrates highlighting of a user's arm in response to a mouse hover over the arm, in accordance with one or more preferred implementations, an interface may be configured to include distinct hotspots for a user's arm and a user's hand, as illustrated in FIG. 10, where a user is hovering over a hand hotspot. FIG. 11 illustrates an indication that a photo or image is associated with the patient's hand.

Figure 12:
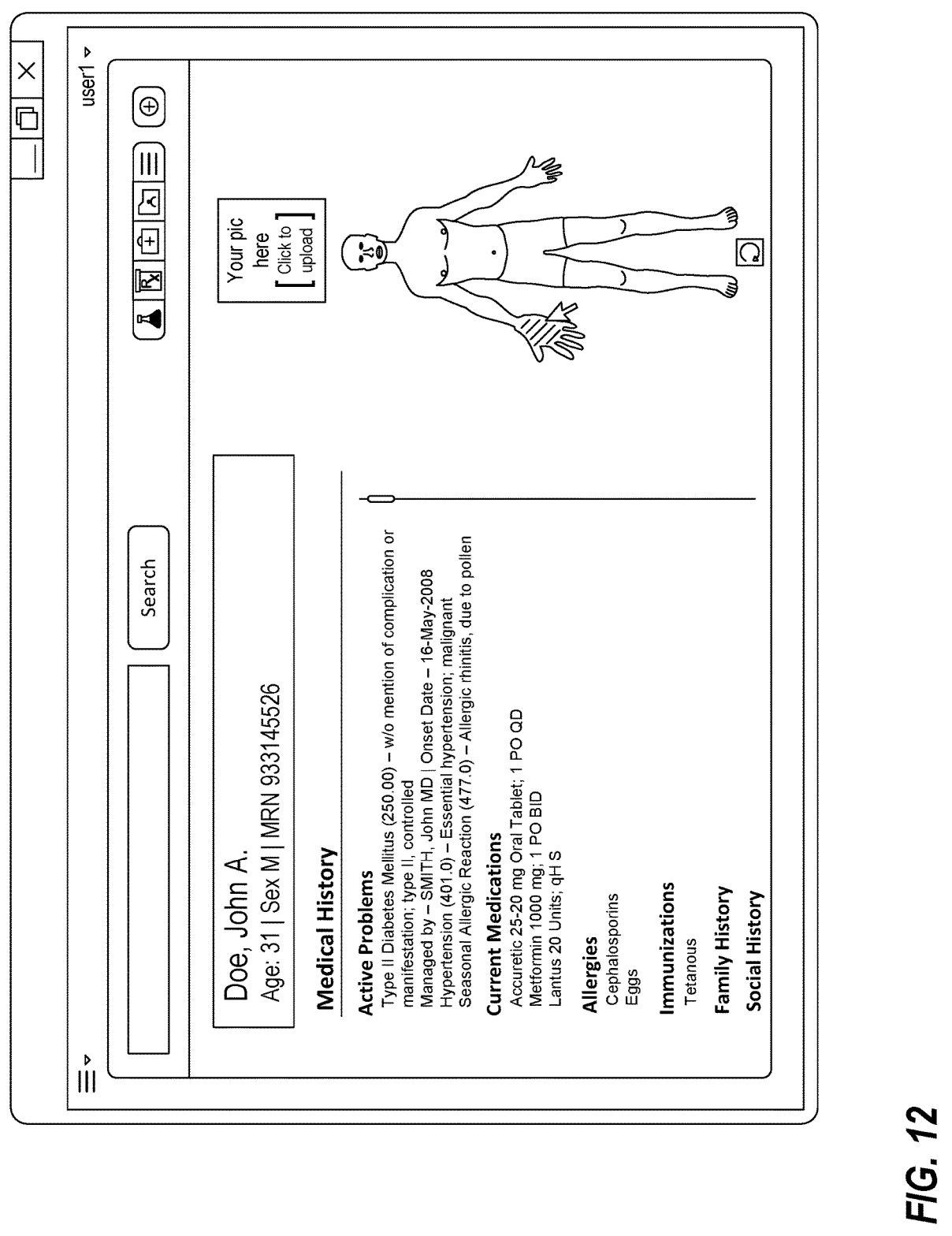
Figure 13:
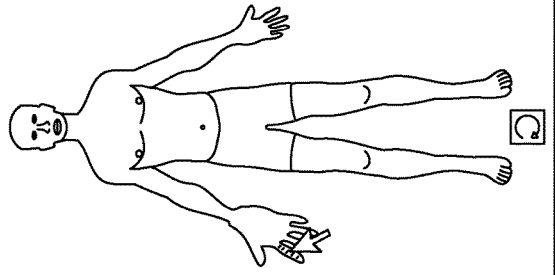

In accordance with one or more preferred implementations, an interface is configured to provide an enlarged and/or enhanced view of a particular portion of an avatar when a user interacts with that portion of the avatar (e.g. by hovering, clicking, double clicking, tapping, double tapping, clicking and holding, or pressing and holding), as illustrated in FIG. 12. In accordance with one or more preferred implementations, such an enlarged or enhanced view includes additional hotspots that a user can associate a photo or image with, as illustrated in FIG. 13, where a user is hovering over an index finger hotspot.

Figure 14:
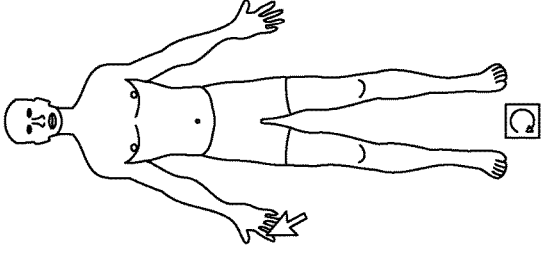

Although functionality is largely described herein in relation to hotspots, in accordance with one or more preferred implementations, a user may even be able to select or indicate a point on an avatar, e.g. for association of a photo or image, as illustrated in FIG. 14.

In accordance with one or more preferred implementations, a callout may be utilized to indicate that one or more photos or images are associated with a hotspot or a particular point of an avatar, as illustrated in FIG. 15.

In accordance with one or more preferred implementations, an electronic healthcare records application is configured to allow a user to select a photo of a patient for association with that patient's electronic healthcare record. FIG. 16 illustrates display of such a photo in an interface of an electronic healthcare records application.

Figure 17:
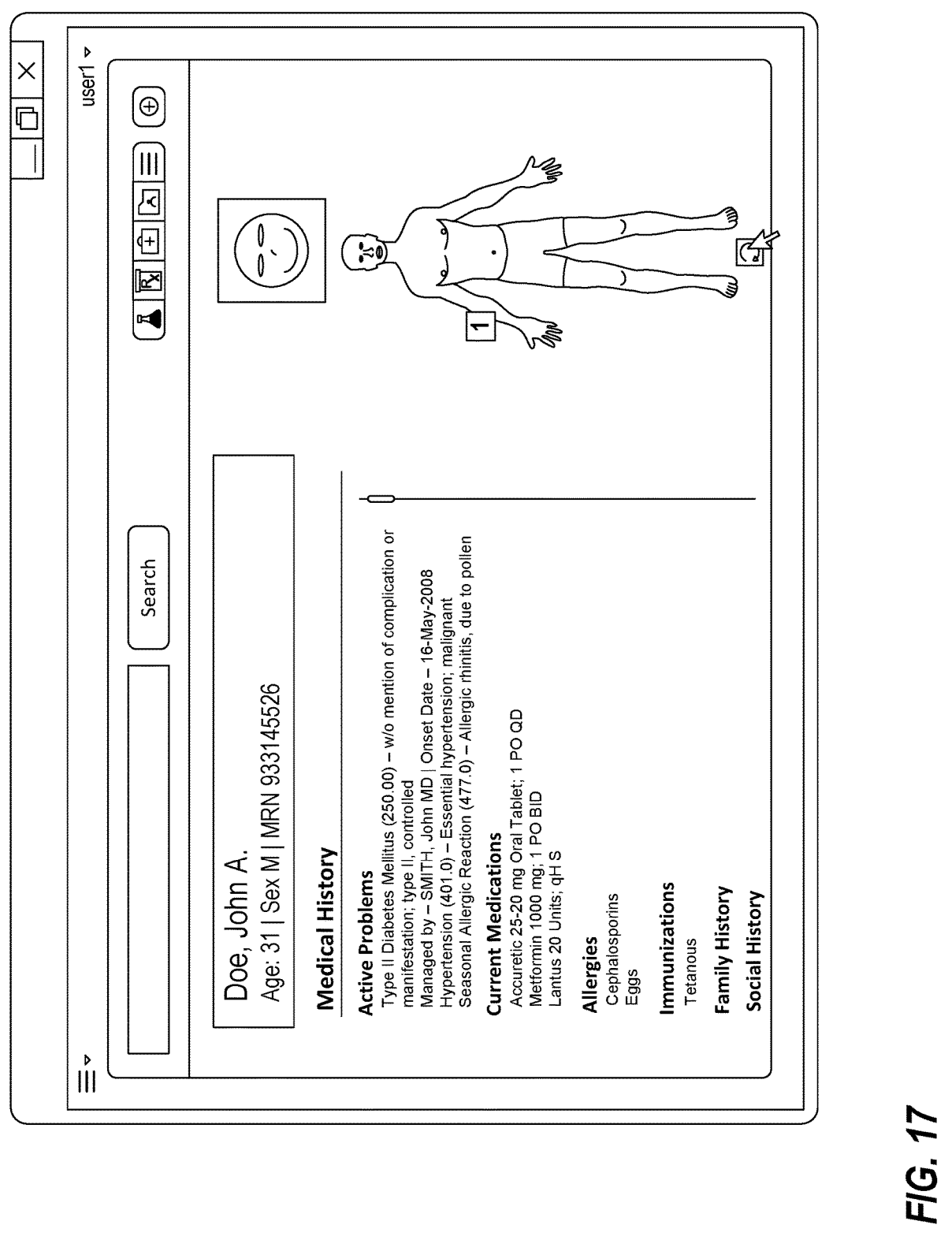

In accordance with one or more preferred implementations, an interface comprising an avatar is configured to allow a user to rotate or reverse the avatar to view the avatar from a different perspective or angle. FIG. 17 illustrates interaction with a user interface element which allows a user to toggle between front and rear views of an avatar. FIG. 18 illustrates display of a rear view of the avatar in response to the user interaction. In accordance with one or more preferred implementations, such functionality allows a user to associate photos or images with a portion of the avatar in either view. In accordance with one or more preferred implementations, additional views or perspectives of an avatar may be utilized, and in accordance with one or more preferred implementations, a user may even be able to rotate a three dimensional avatar in one, two, or even three dimensions.

In accordance with one or more preferred implementations, software provides drag and drop clinical documentation functionality using an anatomical image with hot spots by which one targets the documentation area. Clicking on hot spots can further detail specific anatomic areas (hand, foot, heart, for example), that allows more specific conditions and treatments to be addressed via a drag and drop methodology.

In accordance with one or more preferred implementations, an interface provides fast, intuitive functionality by listing the most common conditions on one side of an anatomical figure, which can be based on a presenting complaint or other directive guidance received upon patient arrival. Preferably, listed items can be dragged onto the appropriate hot spot of the image.

Preferably, the interface provides fast, intuitive functionality by listing correlating common/appropriate treatments for the conditions presented or selected. Preferably, listed treatment items can be dragged onto the appropriate hot spot of the image In accordance with one or more preferred implementations, software provides drill down capability which allows a user to drill down to more specific anatomical areas for more specific documentation. Preferably, hot spots on a figure or image can be further detailed by double-clicking or some other selection method before documenting. For example, a user can drill in on the chest down to the heart or further to the heart chambers, veins, arteries, etc. In accordance with one or more preferred implementations, drill down functionality is customized for medical specialties such as cardiac, obstetrical, hand, foot, etc.

Figure 19:
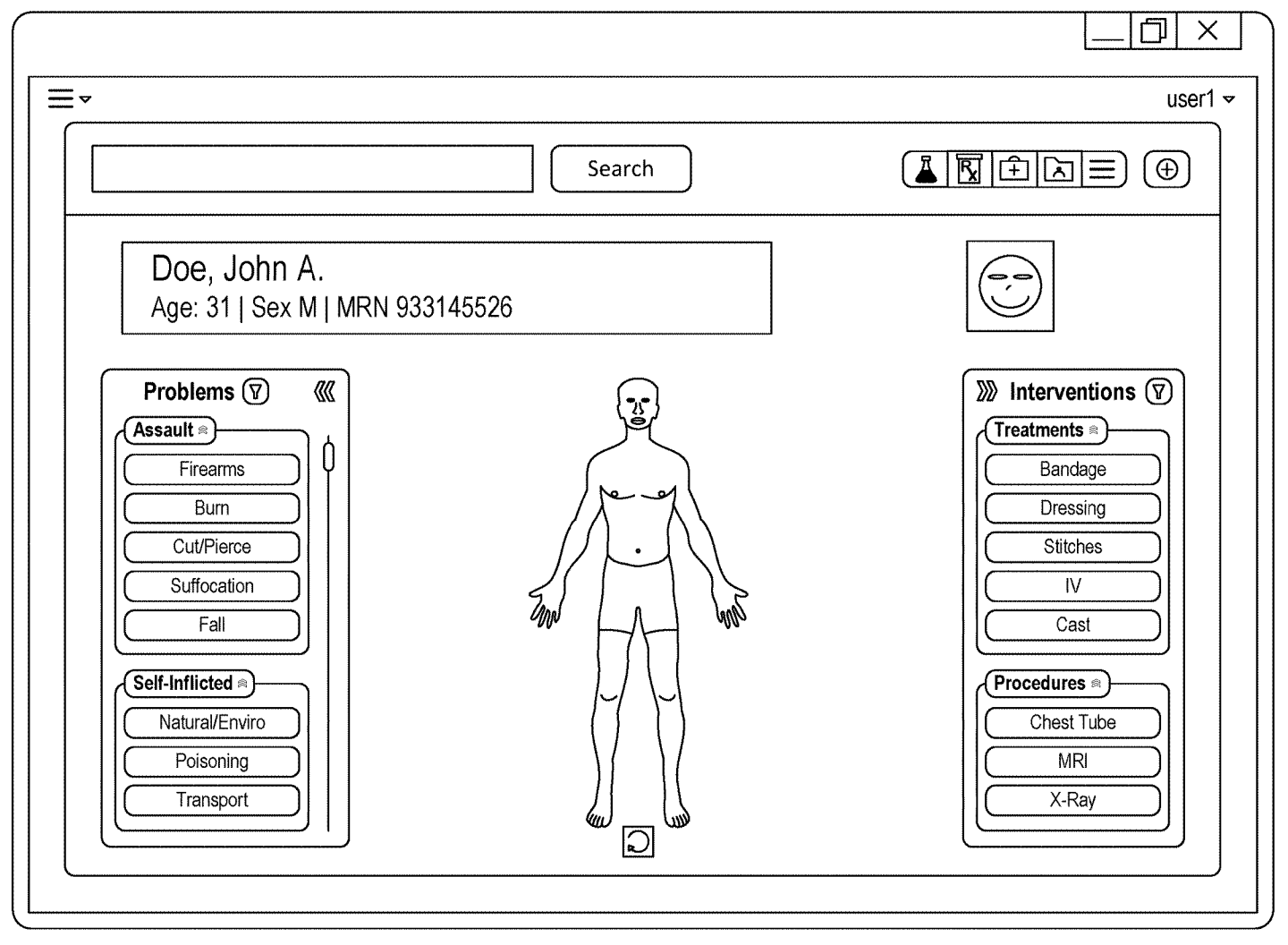

FIG. 19 illustrates an exemplary interface in accordance with one or more preferred implementations. The exemplary interface includes a listing of problems and interventions that can be dragged onto an avatar for the purpose of clinical documentation for a patient. In accordance with one or more preferred implementations, the items included in the listings, as well as headings, groupings, and subheadings of the listings, can be customized by an administrative user. In accordance with one or more preferred implementations, a user can filter displayed items.

Figure 20:
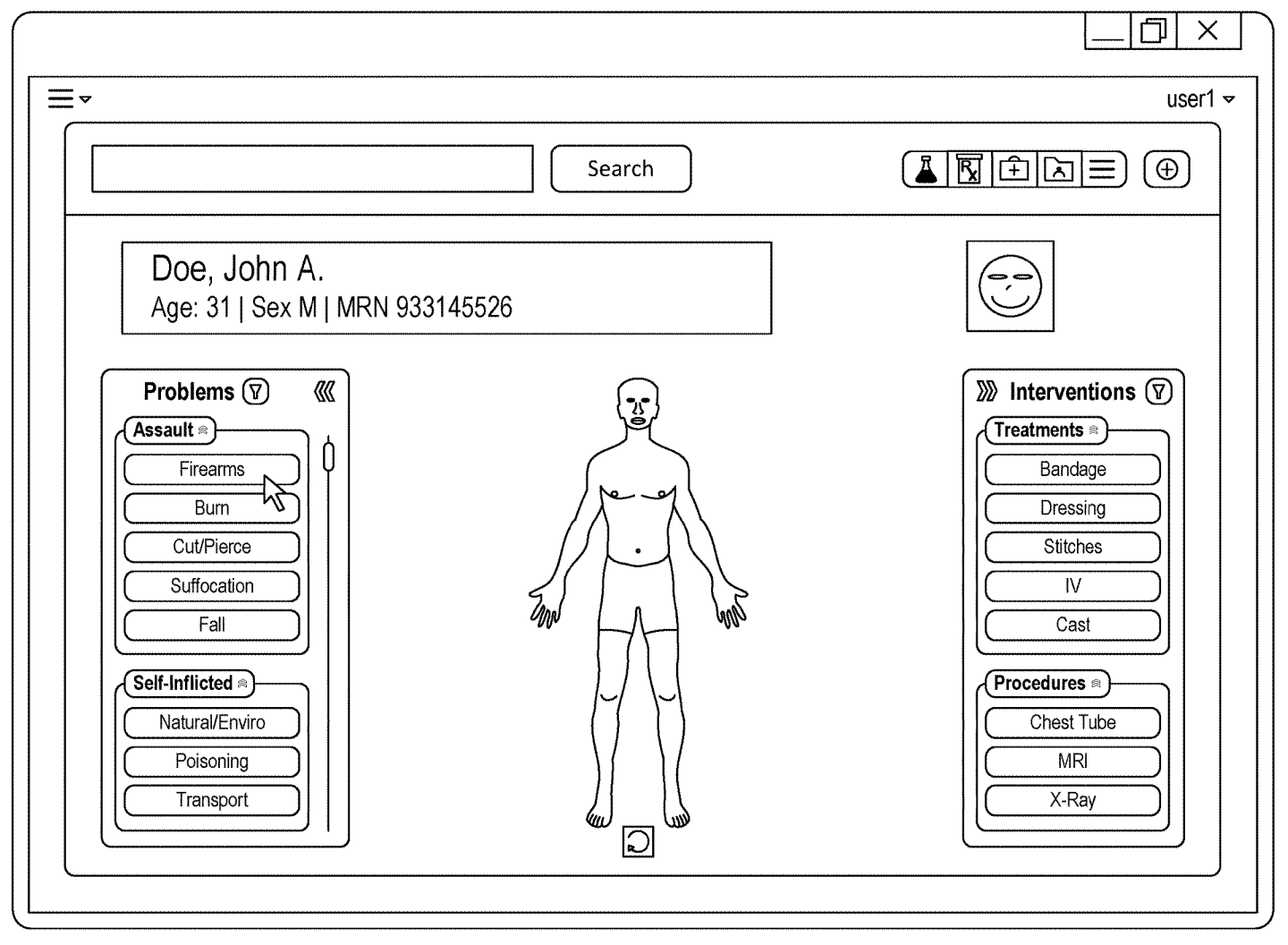
Figure 21:
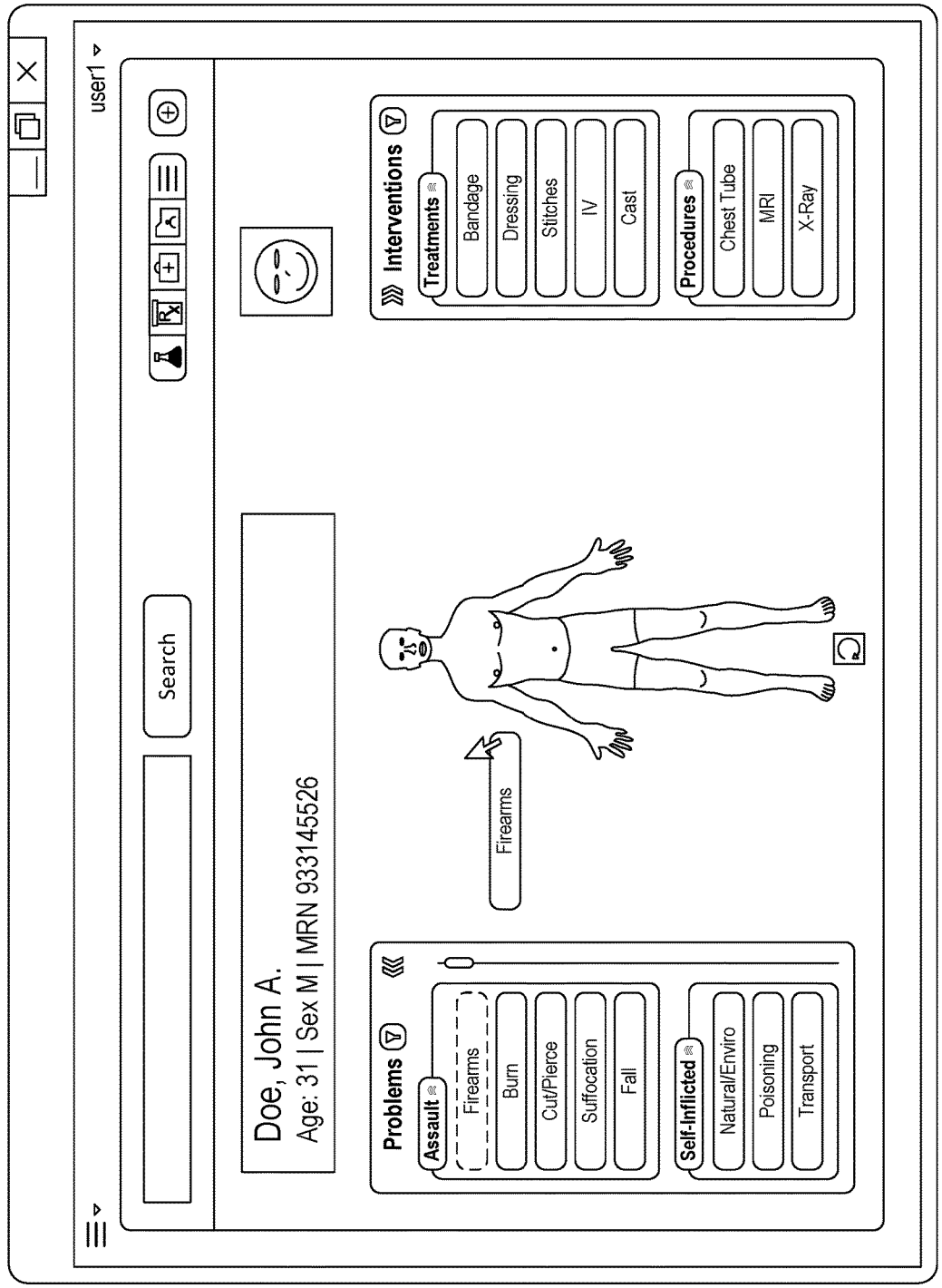
Figure 22:
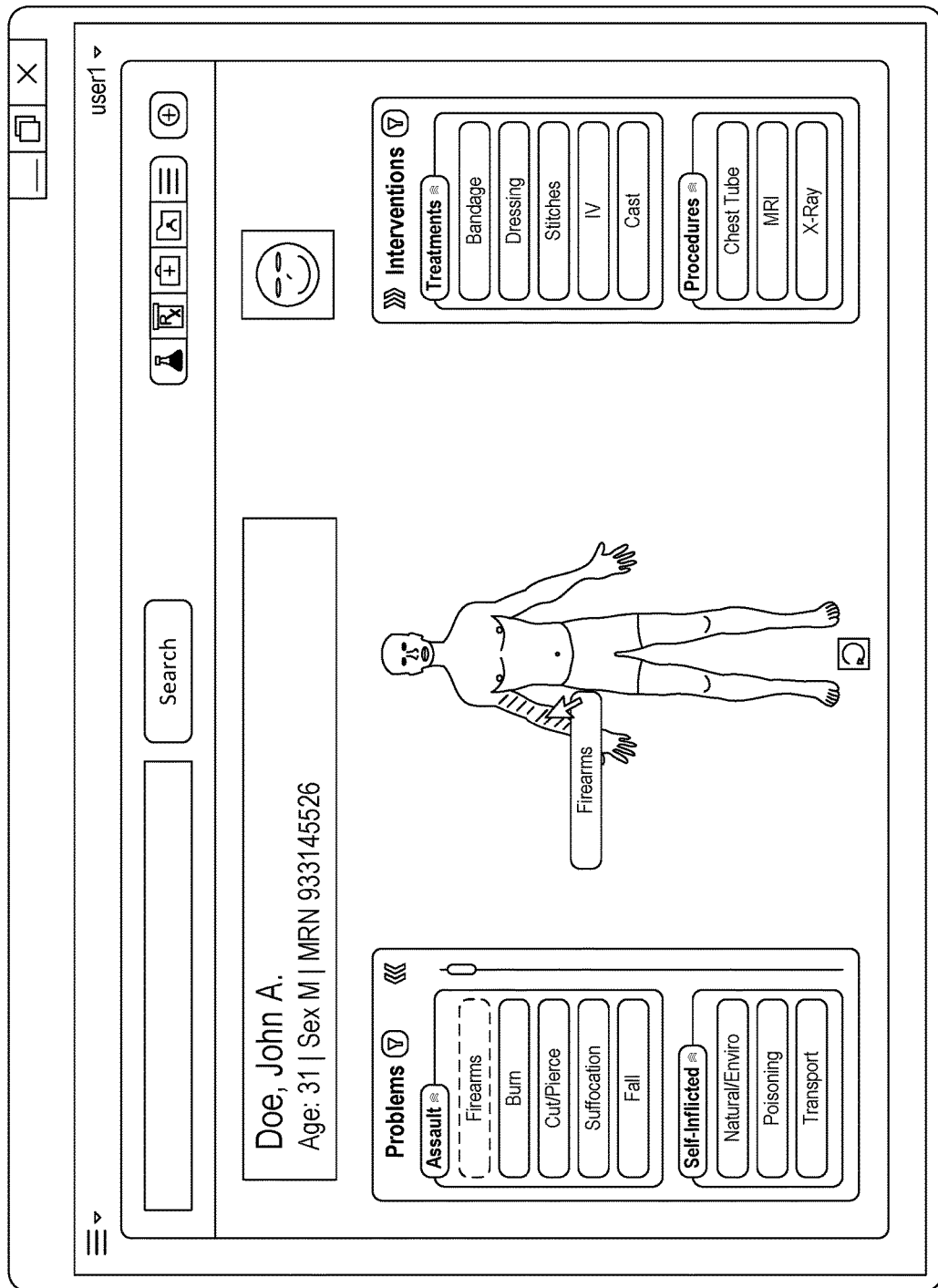
Figure 23:
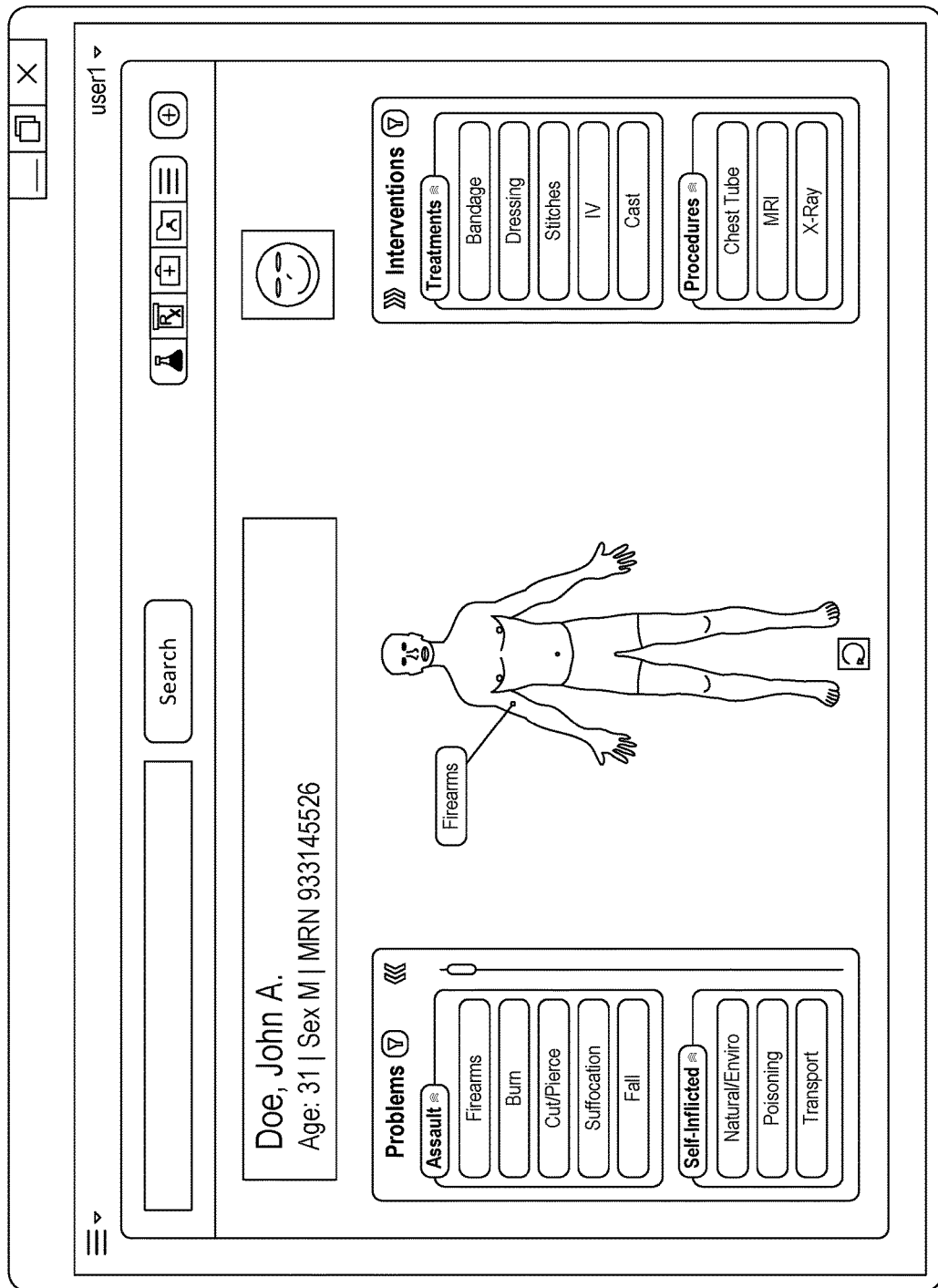
FIG. 23 illustrates display of a firearms problem item in association with an avatar.

FIGS. 20-22 illustrate dragging of a firearms problem item onto an arm hotspot of the avatar. This results in a firearms problem item being displayed as associated with the arm hotspot, as illustrated in FIG. 23.

Figure 24:
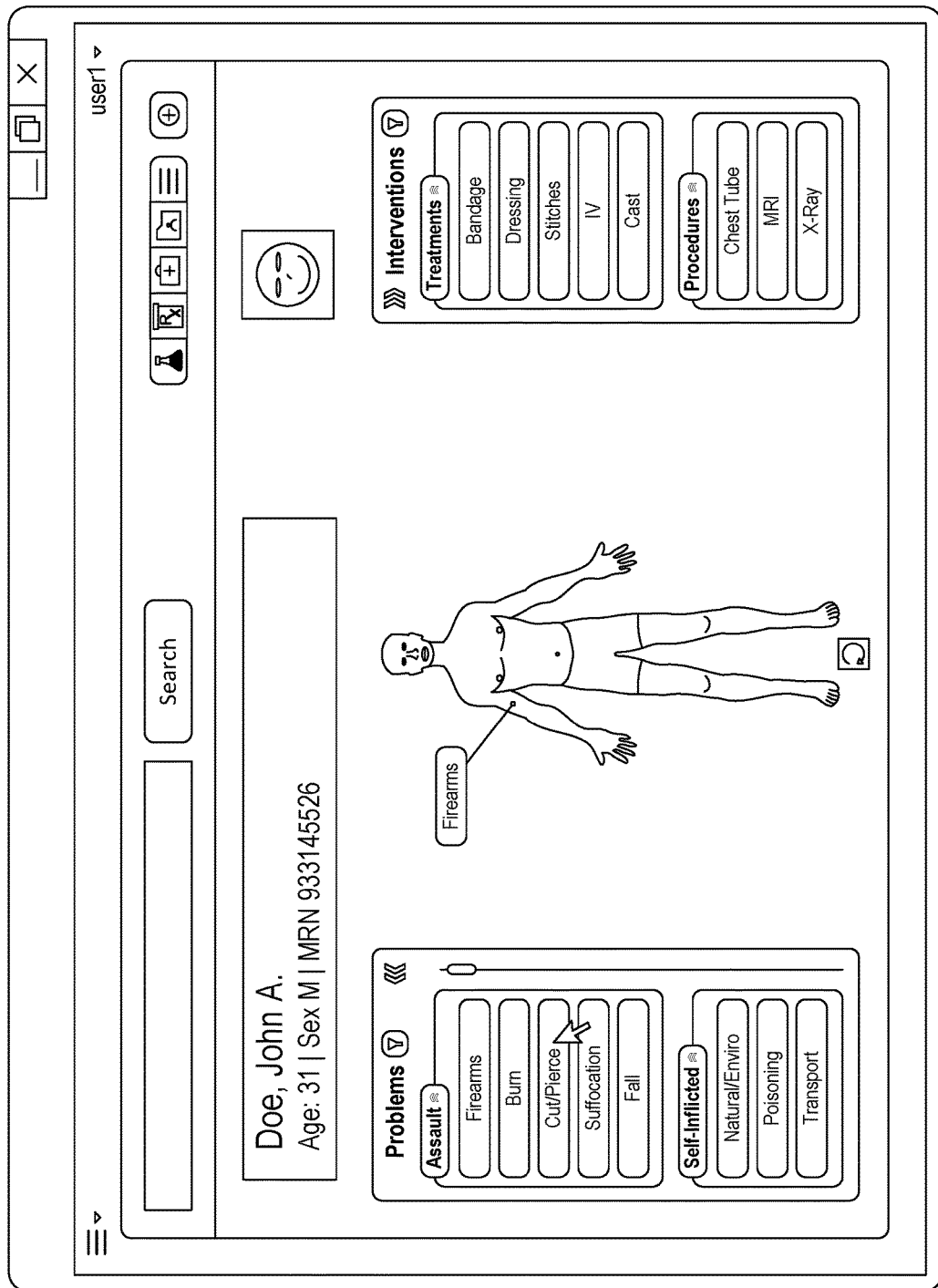
FIGS. 24-26 illustrate how dragging and hovering of a cut/pierce problem item over a hand of an avatar results in an enlarged view of the hand which allows a user to drop the cut/pierce problem item onto an index finger portion of the avatar.
Figure 25:
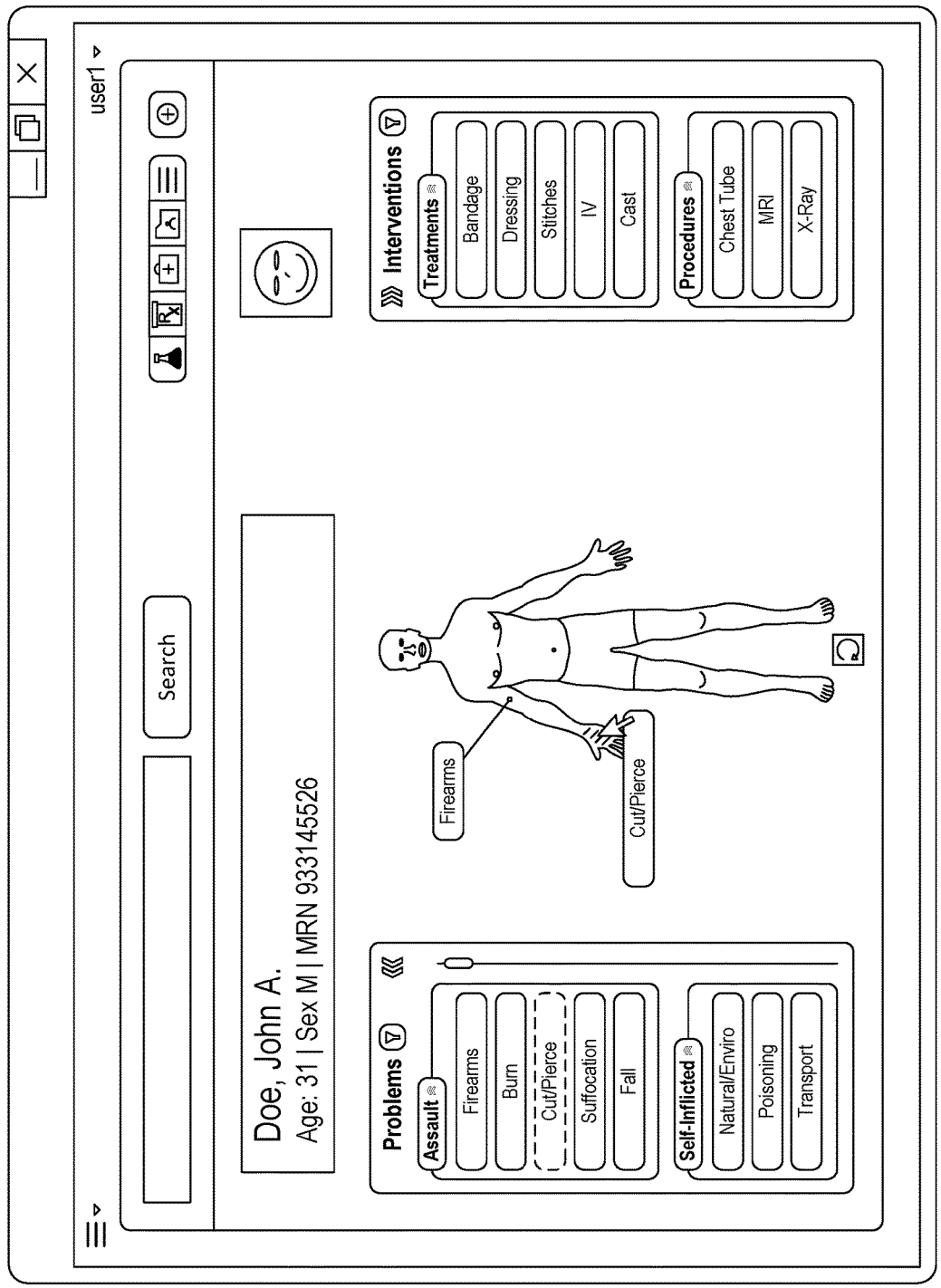
Figure 26:
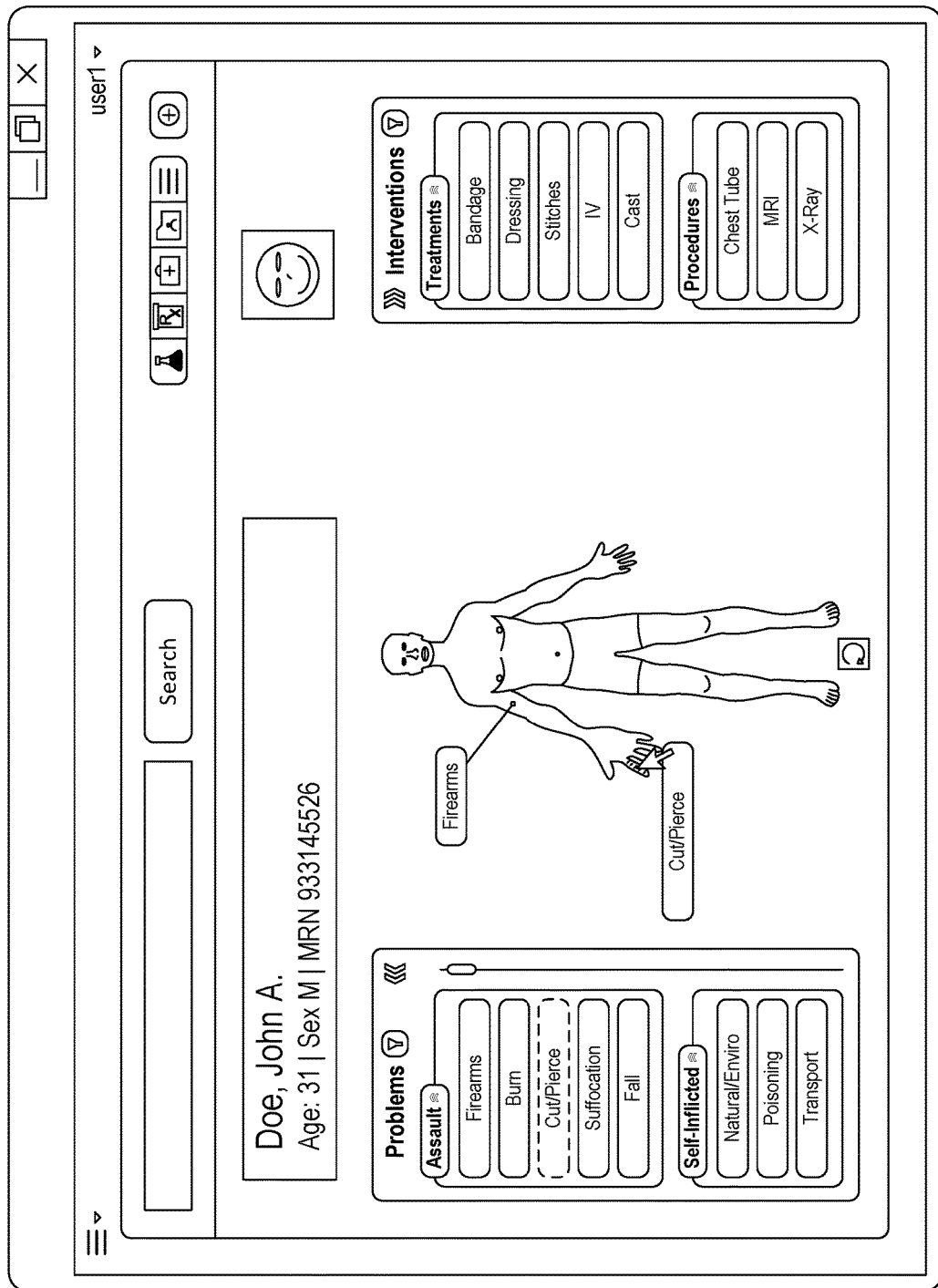

In accordance with one or more preferred implementations, the interface is configured to provide an enlarged and/or enhanced view of a particular portion of the avatar when a user interacts with that portion of the avatar (e.g. by hovering, clicking, double clicking, tapping, double tapping, clicking and holding, or pressing and holding). FIGS. 24-25 illustrate dragging and hovering of a cut/pierce problem item over a hand of the avatar, resulting in an enlarged view of the hand which allows a user to drop the cut/pierce problem item onto an index finger hotspot, as illustrated in FIG. 26.

Figure 27:
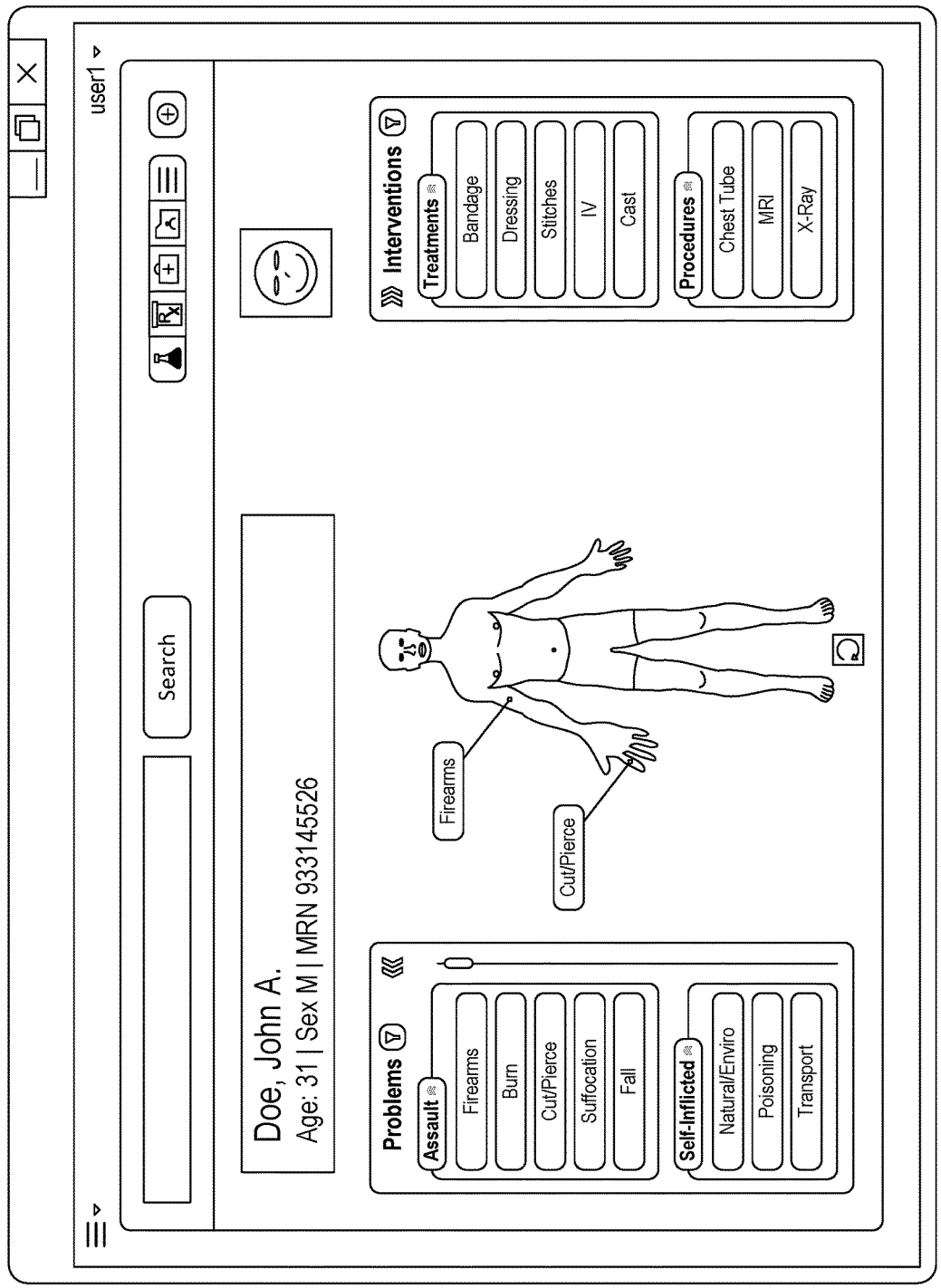
Figure 28:
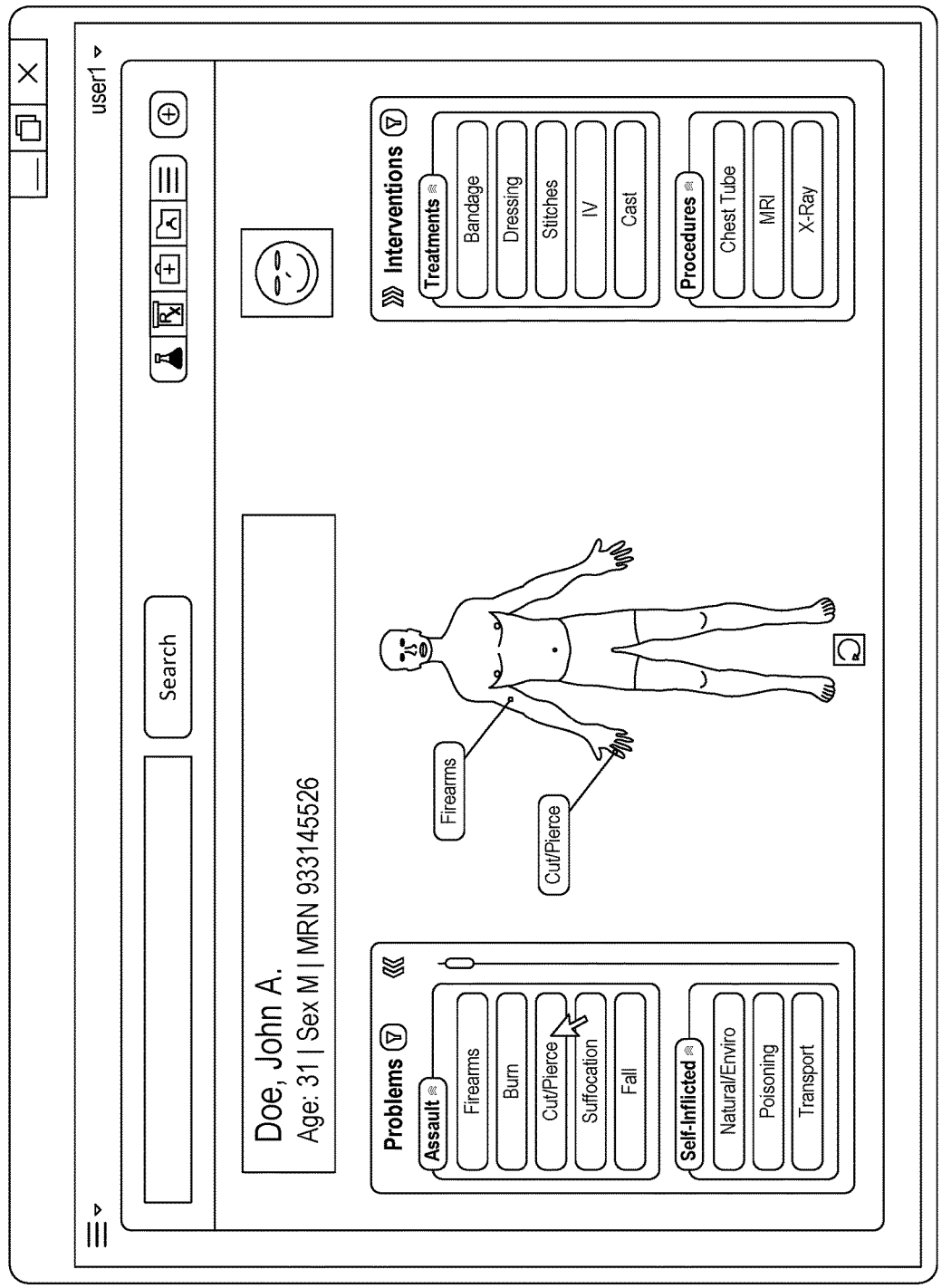
Figure 29:
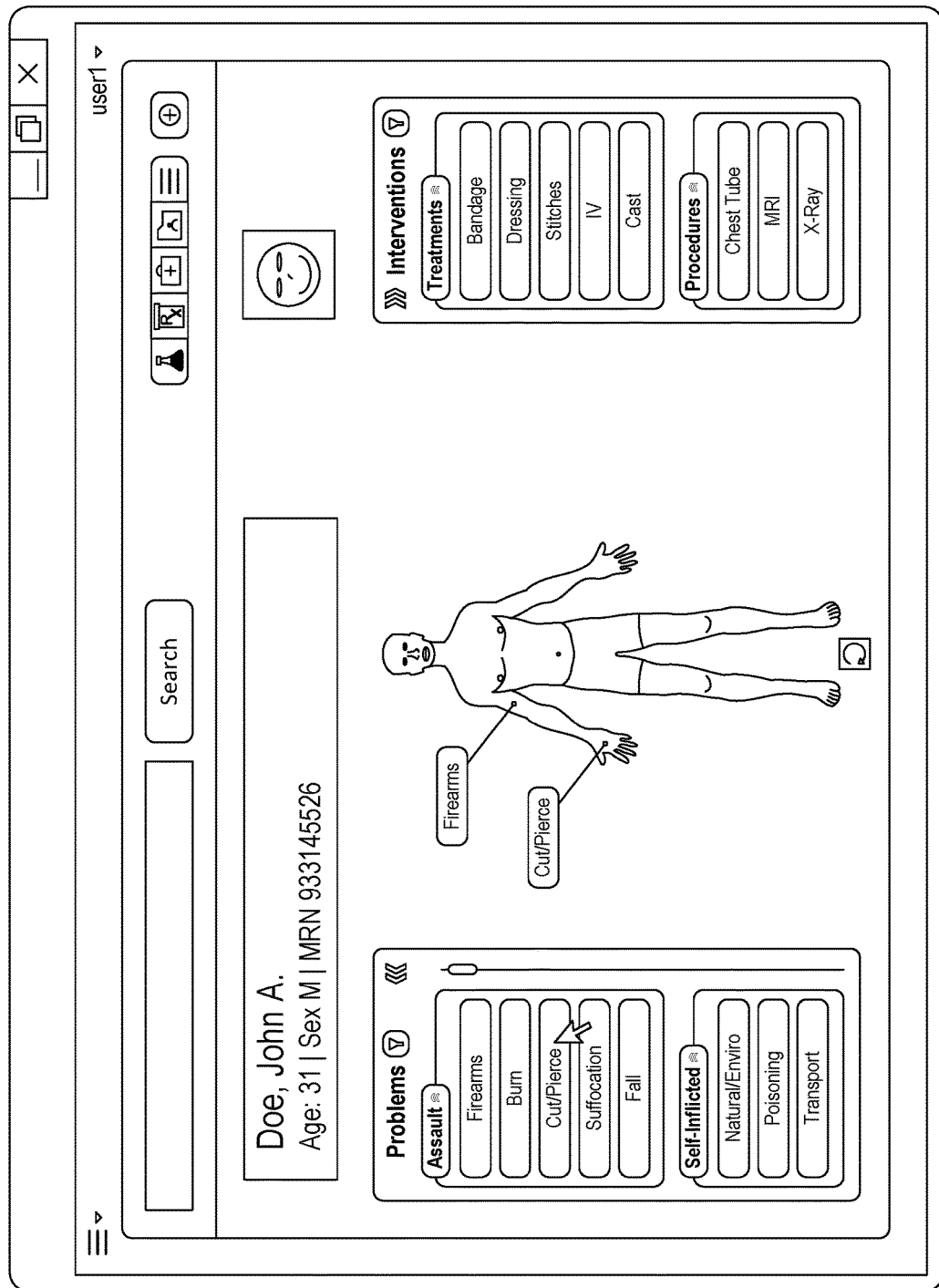

In accordance with one or more preferred implementations, once an item has been associated with a specific hotspot in an enlarged and/or enhanced view, that enlarged and/or enhanced view may continue to be displayed, as illustrated in FIG. 27. Alternatively, the enlarged and/or enhanced view may no longer be displayed, as illustrated in FIG. 28. In accordance with one or more preferred implementations, an item associated with a hotspot in an enlarged and/or enhanced view may simply be displayed as associated with a more general area until that enlarged and/or enhanced view is accessed, as illustrated in FIG. 29. In accordance with one or more preferred implementations, an enlarged and/or enhanced view may be accessed by hovering, clicking, double clicking, tapping, double tapping, clicking and holding, or pressing and holding on a portion of an avatar.

Figure 30:
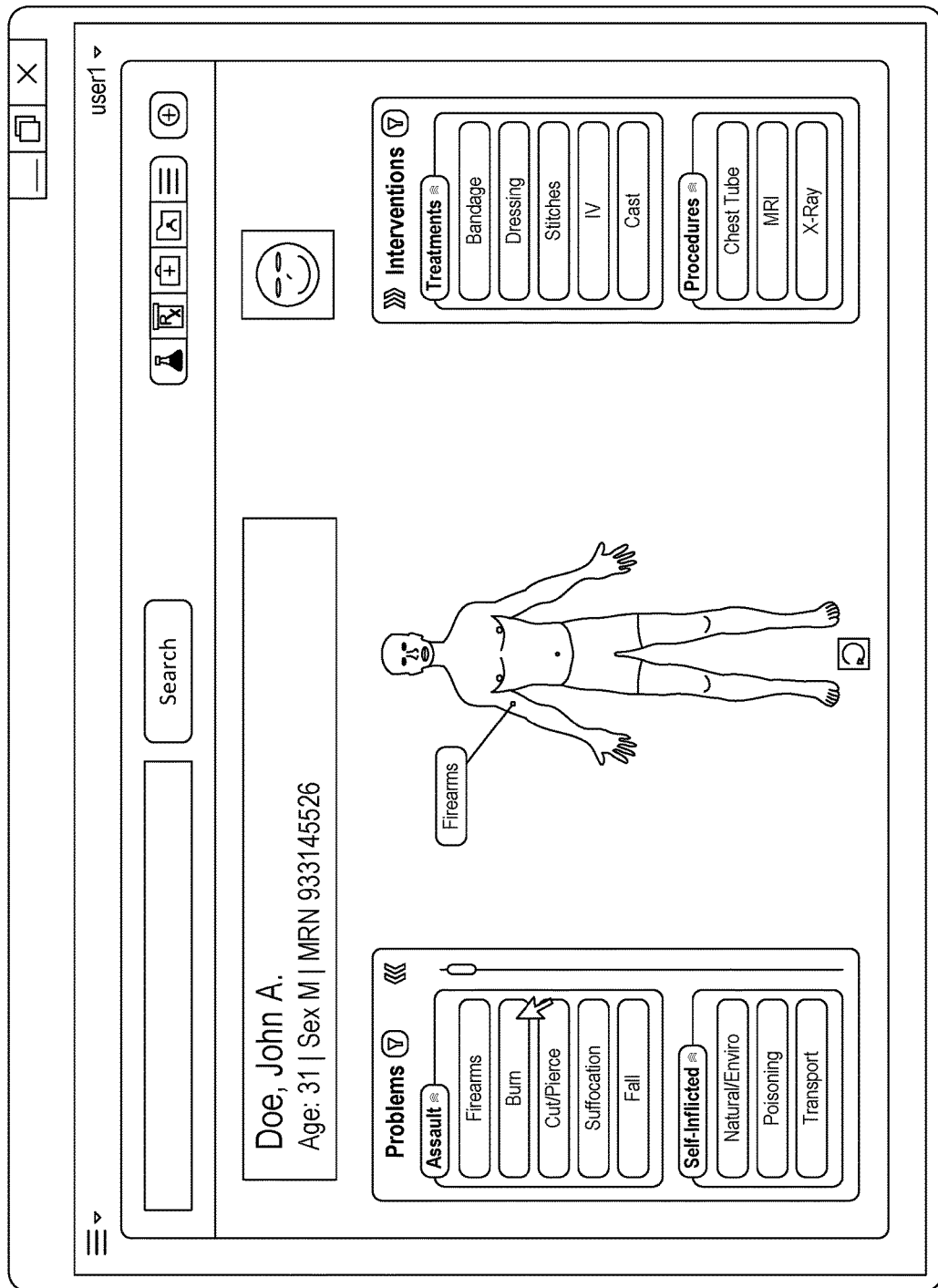
Figure 31:
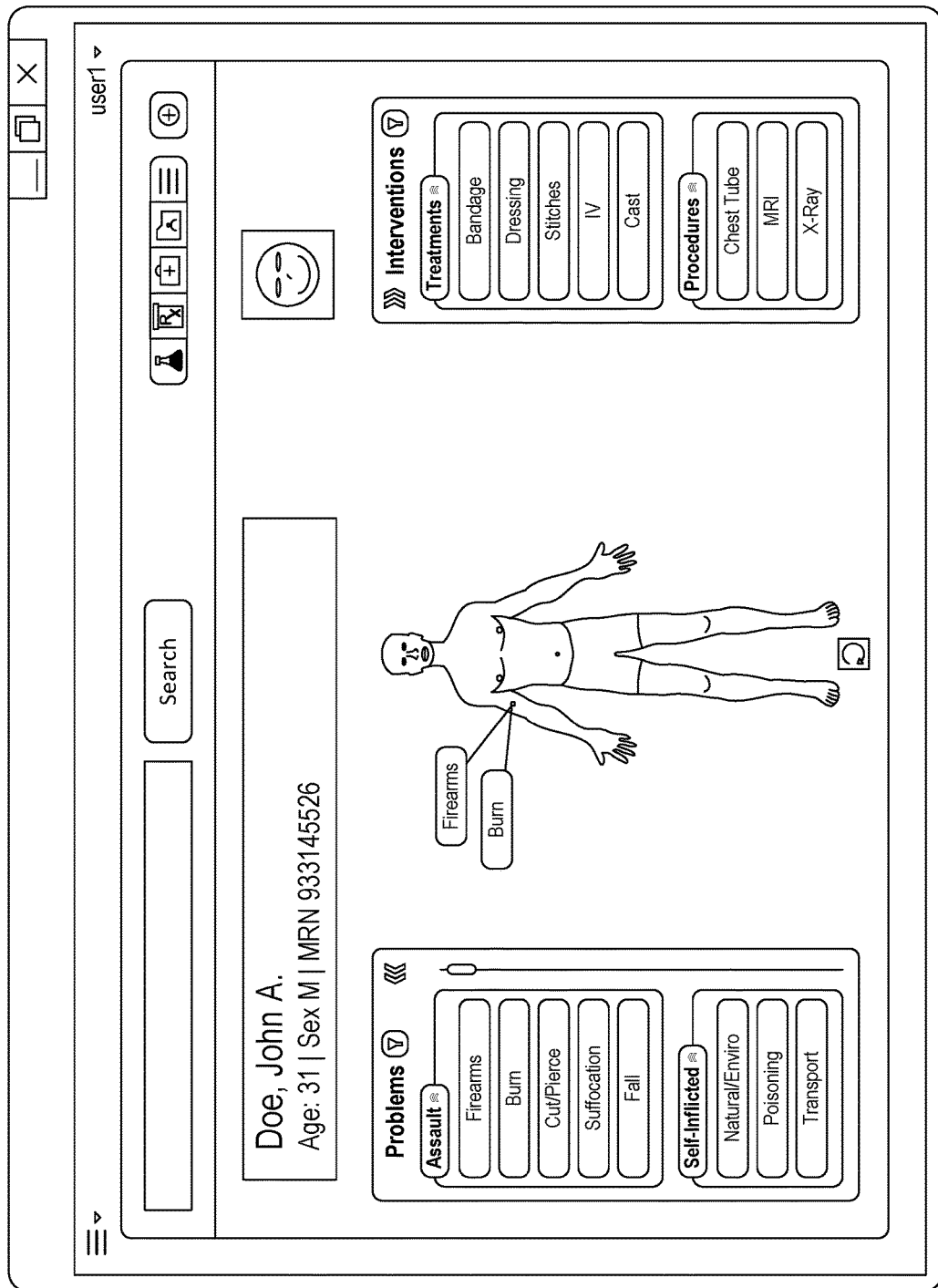

In accordance with one or more preferred implementations, a user can associate multiple items with a single hotspot. FIGS. 30-31 illustrates association of a burn problem item with the right arm hotspot with which a firearms problem item was already associated. In accordance with one or more preferred implementations, an interface is configured to utilize only a single connection point for multiple items attached to the same hotspot, as illustrated in FIG. 31.

Figure 32:
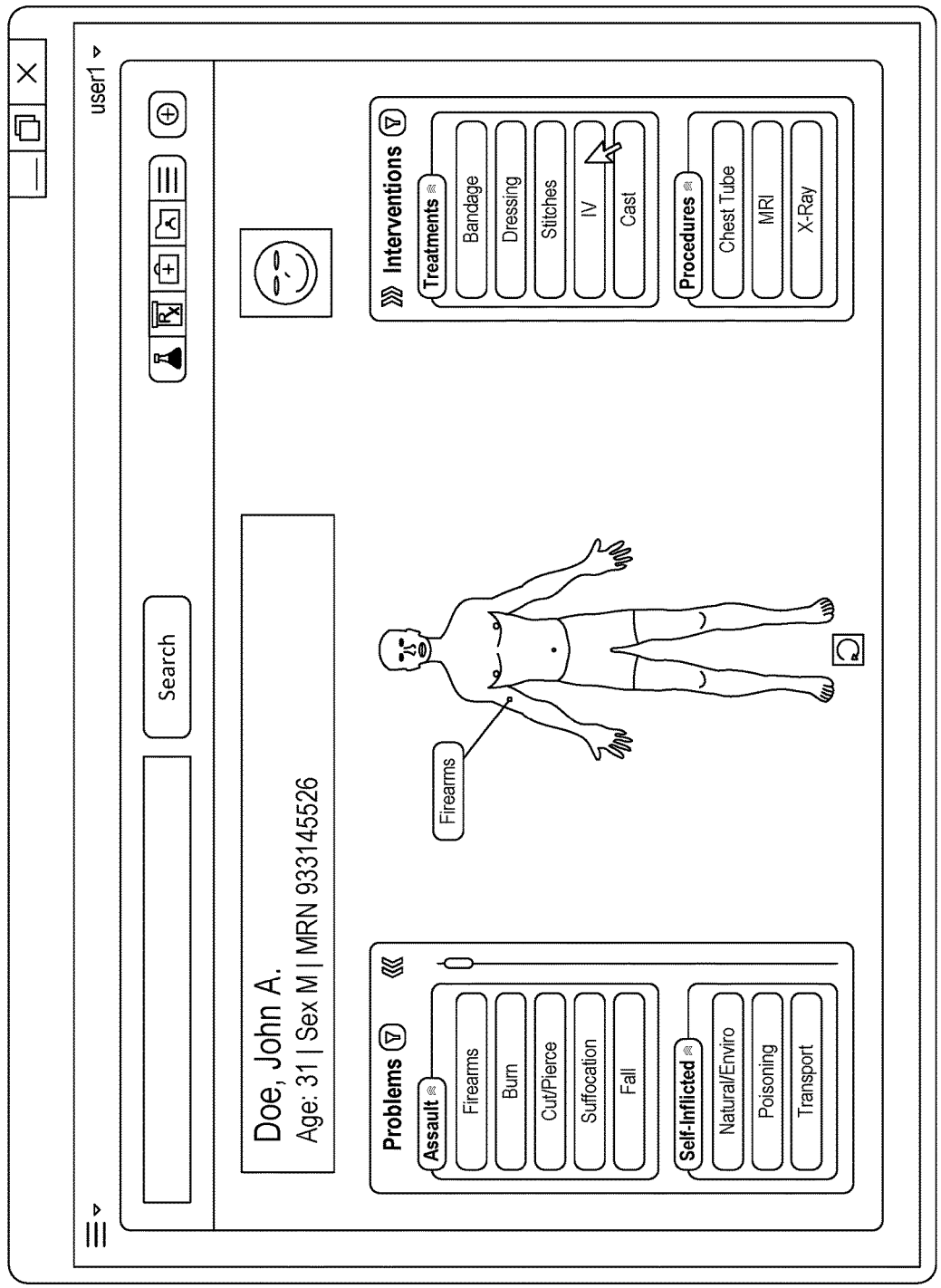
Figure 33:
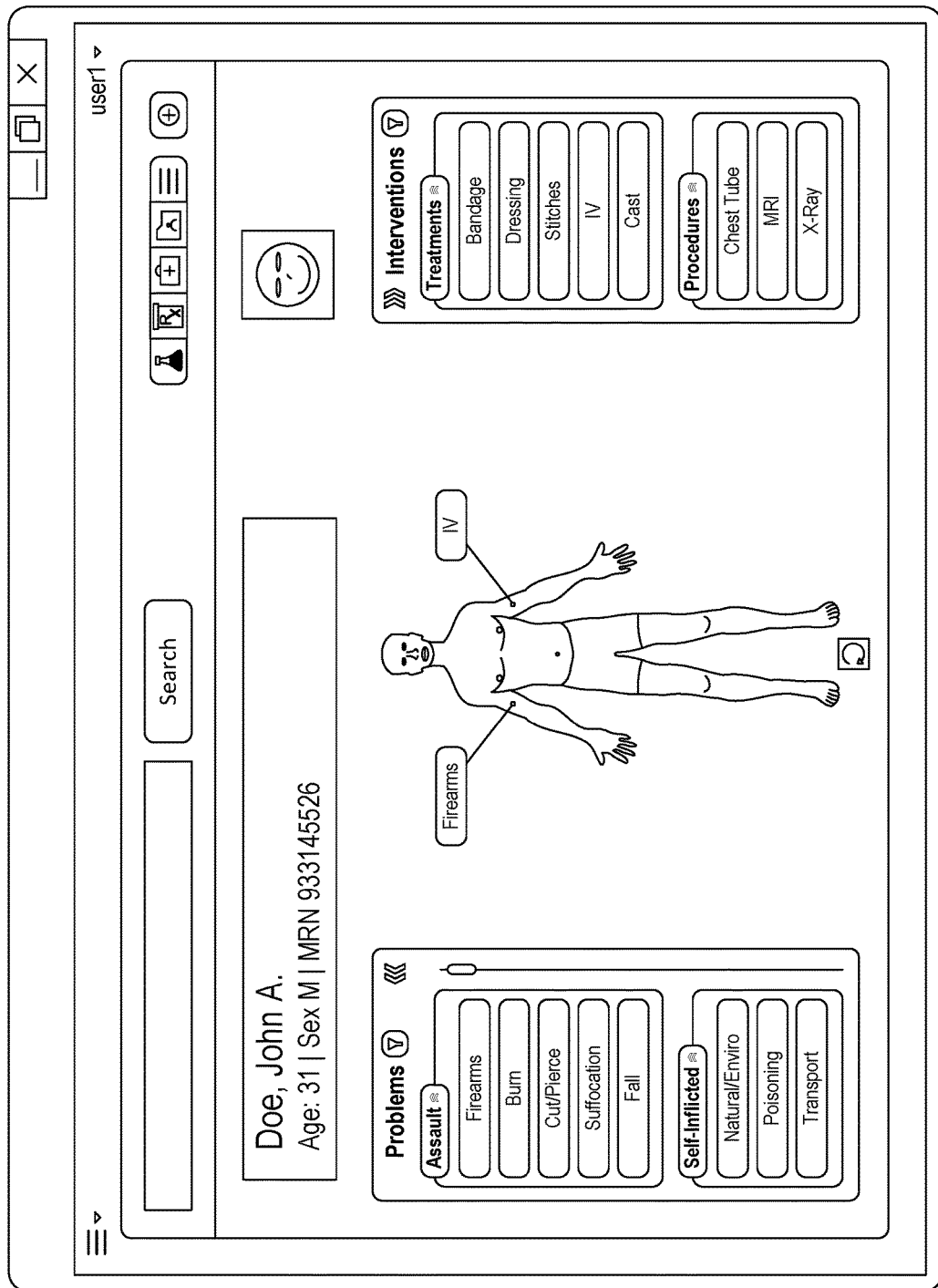

In accordance with one or more preferred implementations, a user can utilize the interface of FIG. 19 to document both problems and interventions for a patient. FIGS. 32-33 illustrate association of an IV intervention item with a left arm hotspot.

Figure 34:
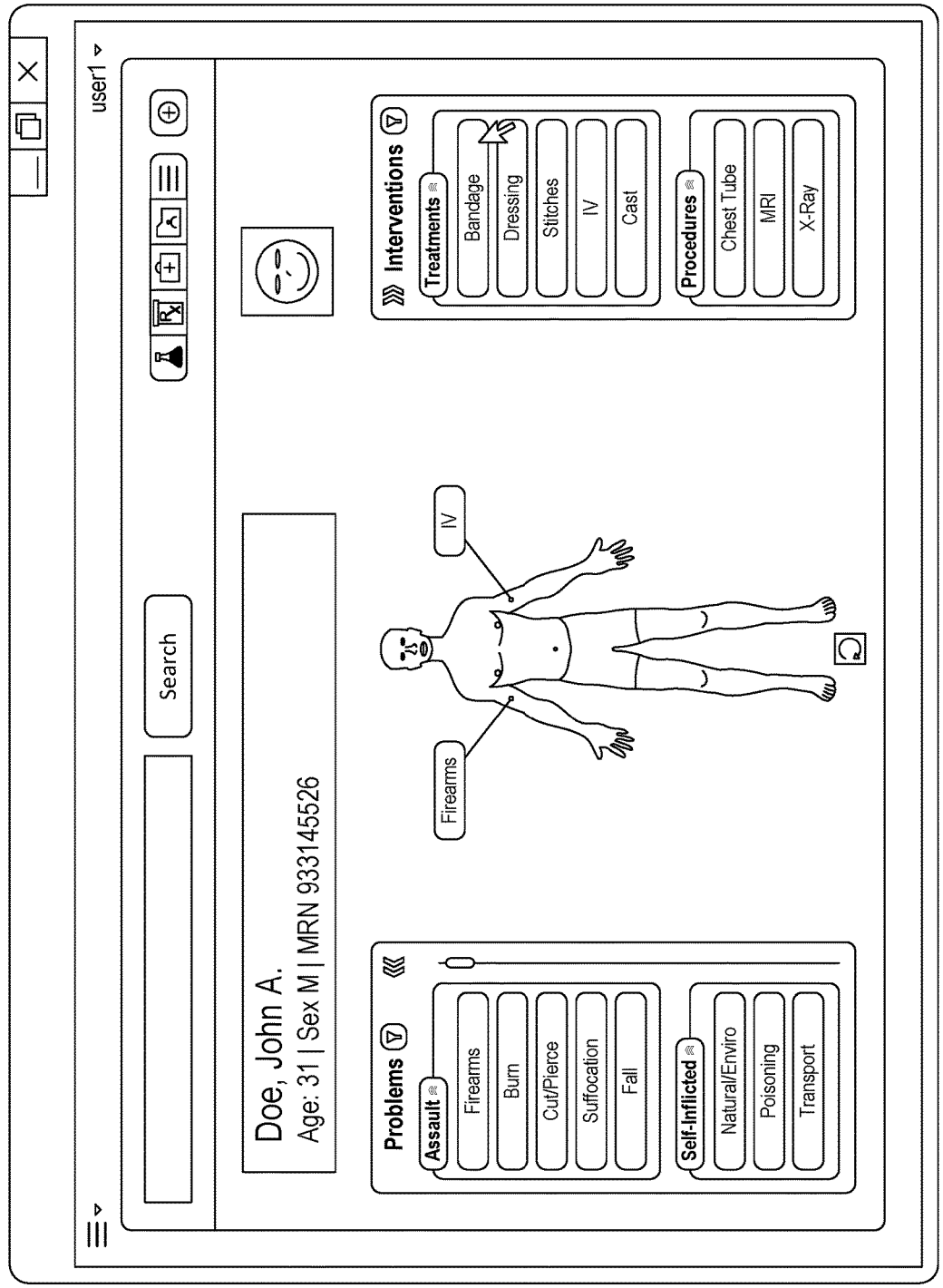
Figure 35:
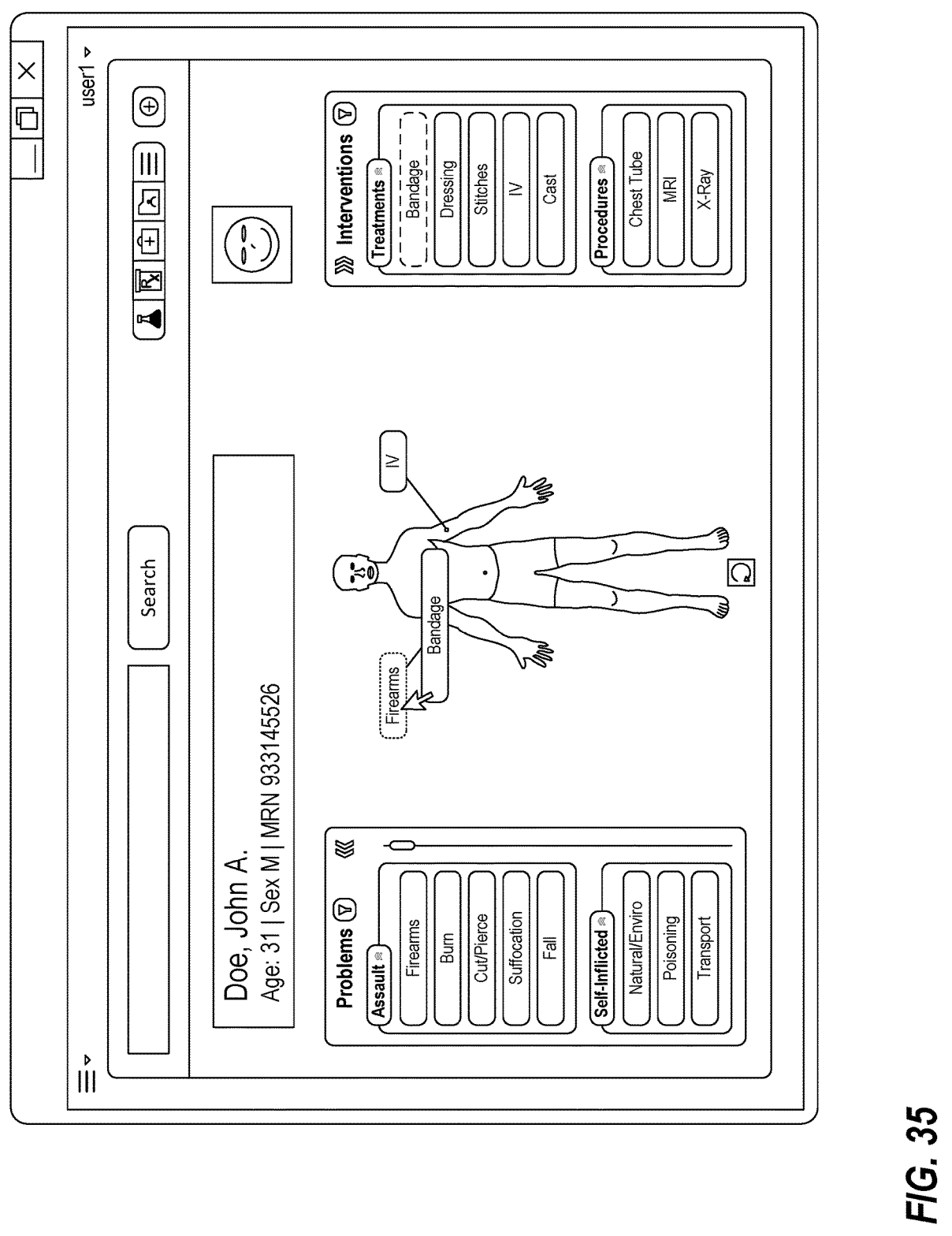
Figure 36:
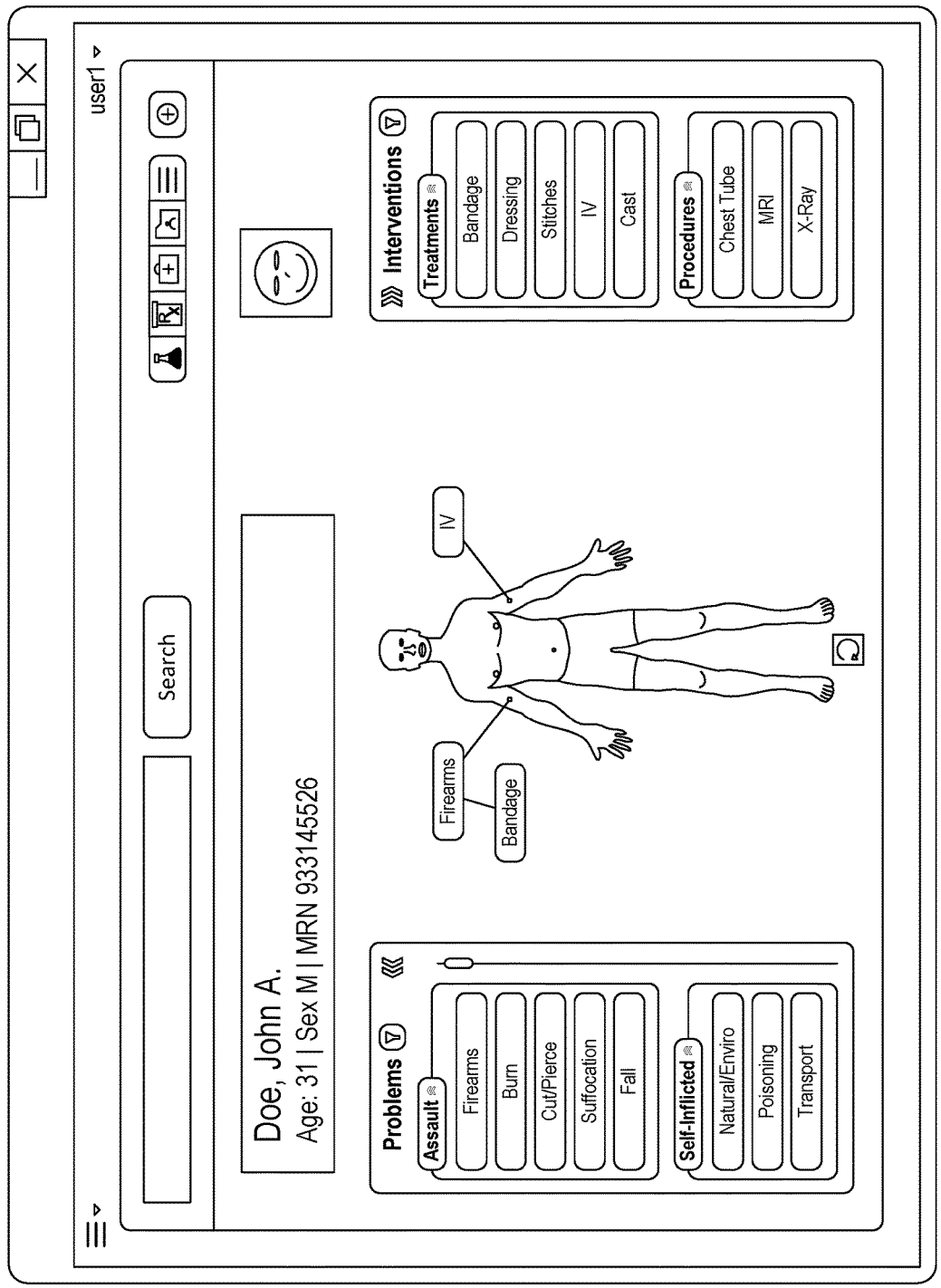
Figure 37:
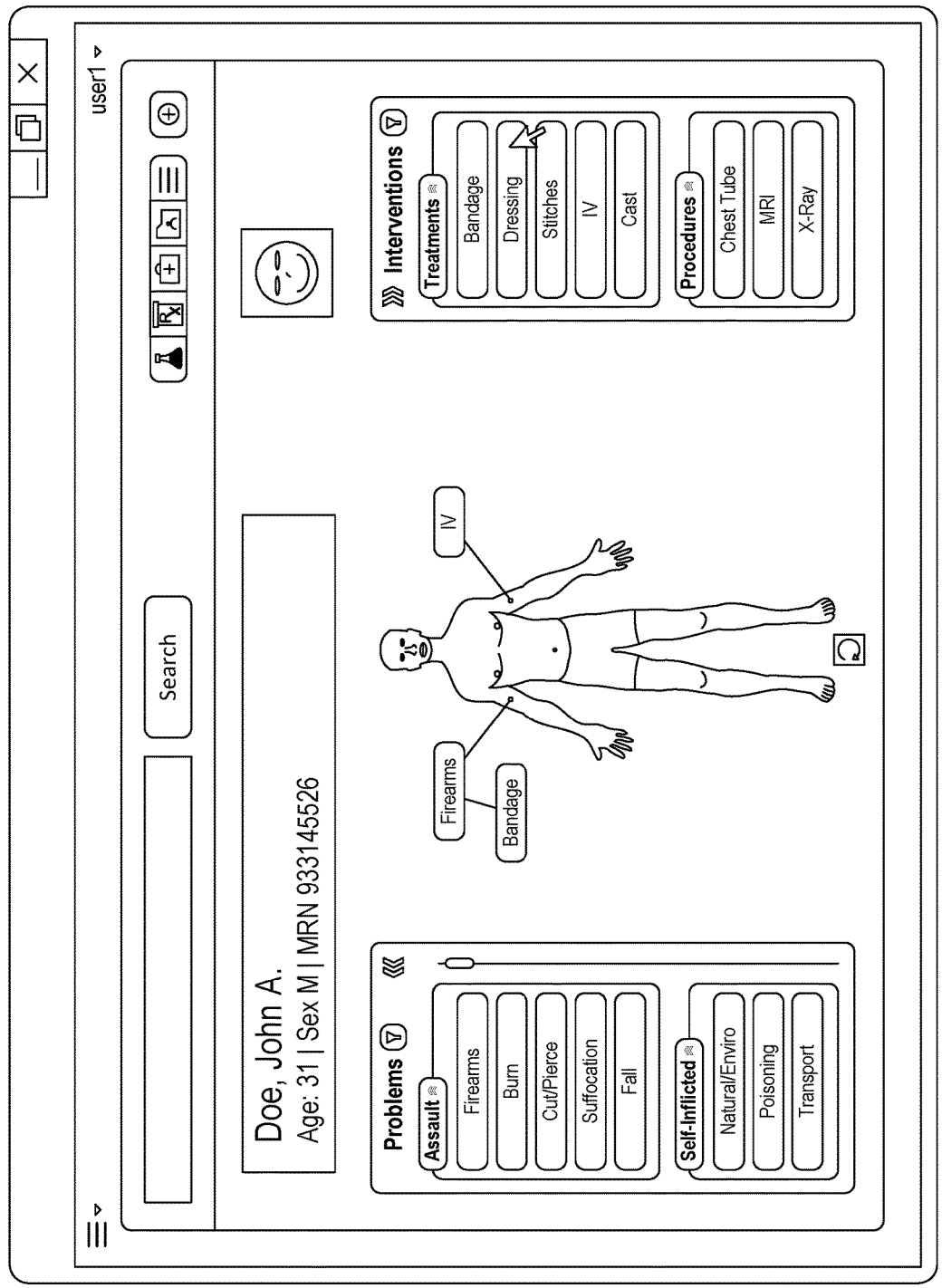
Figure 38:
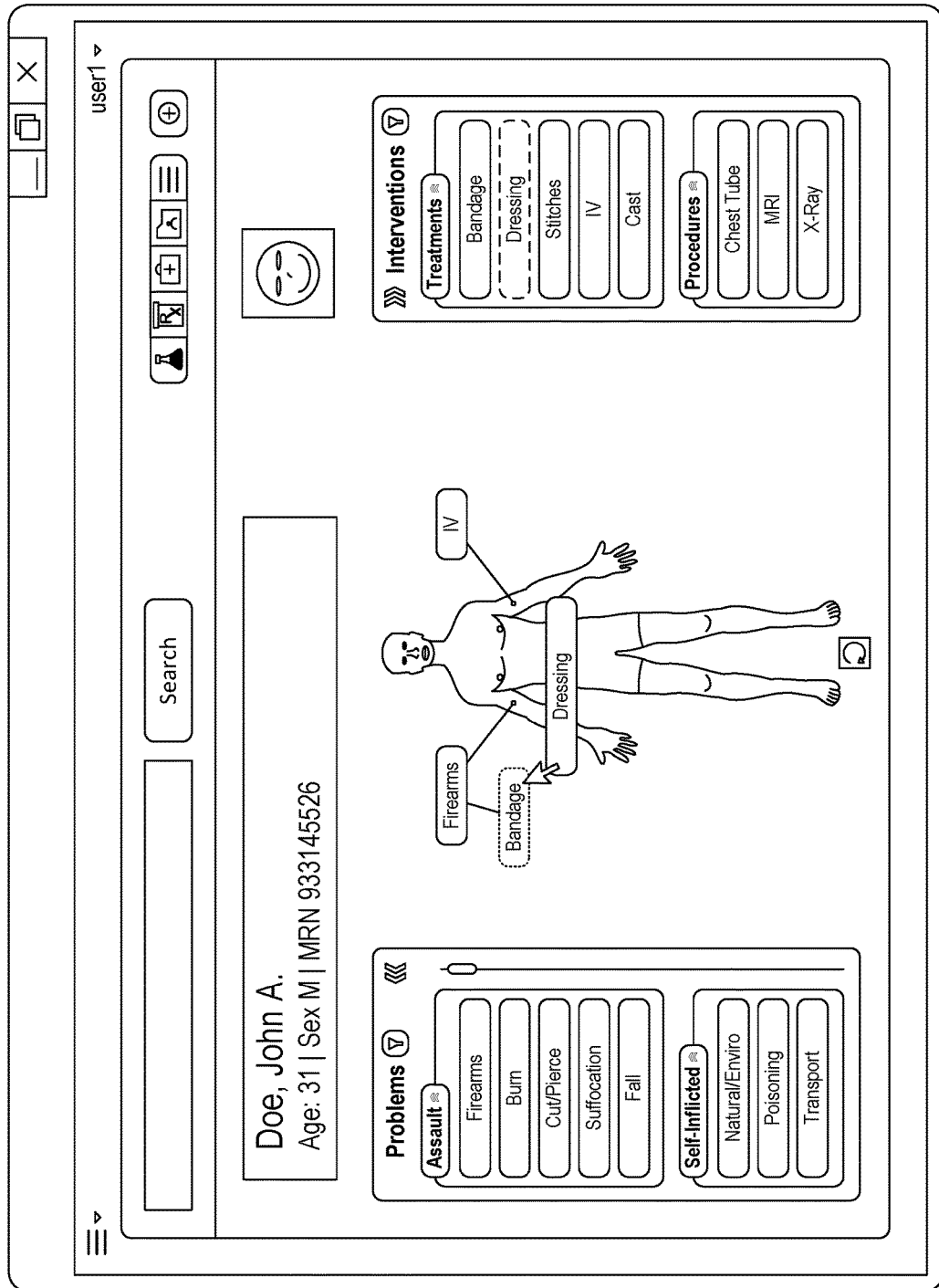
Figure 39:
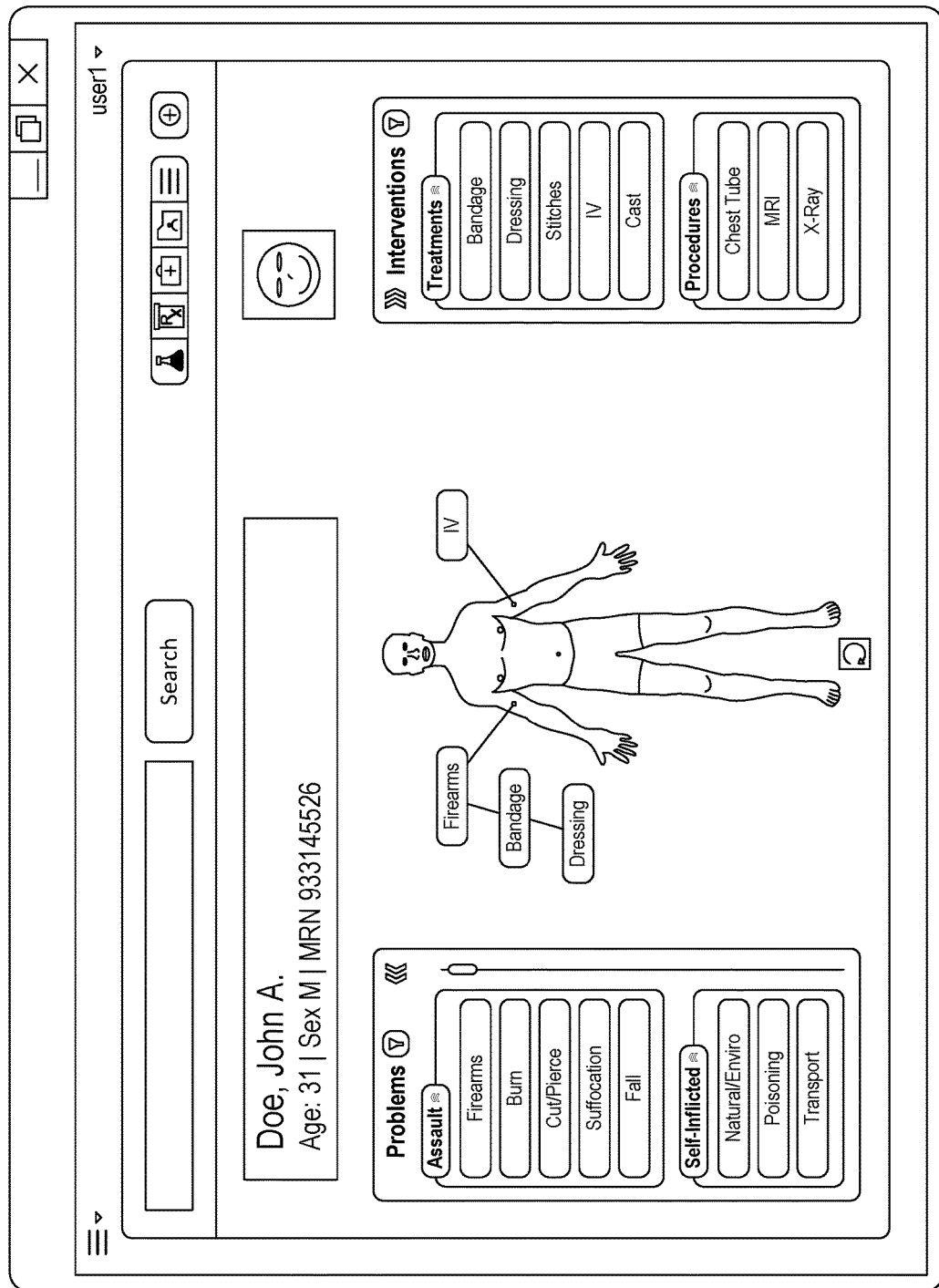

In accordance with one or more preferred implementations, a user can associate, or link, items not just with avatar hotspots, but also with other items associated with the avatar. For example, FIGS. 34-36 illustrate linking of a bandage intervention item with the firearms problem item. In accordance with one or more preferred implementations, multi-level linkage or association is permitted. For example, FIGS. 37-39 illustrate linkage of a dressing intervention item with the bandage intervention item that is itself linked with the firearms problem item.

Figure 40:
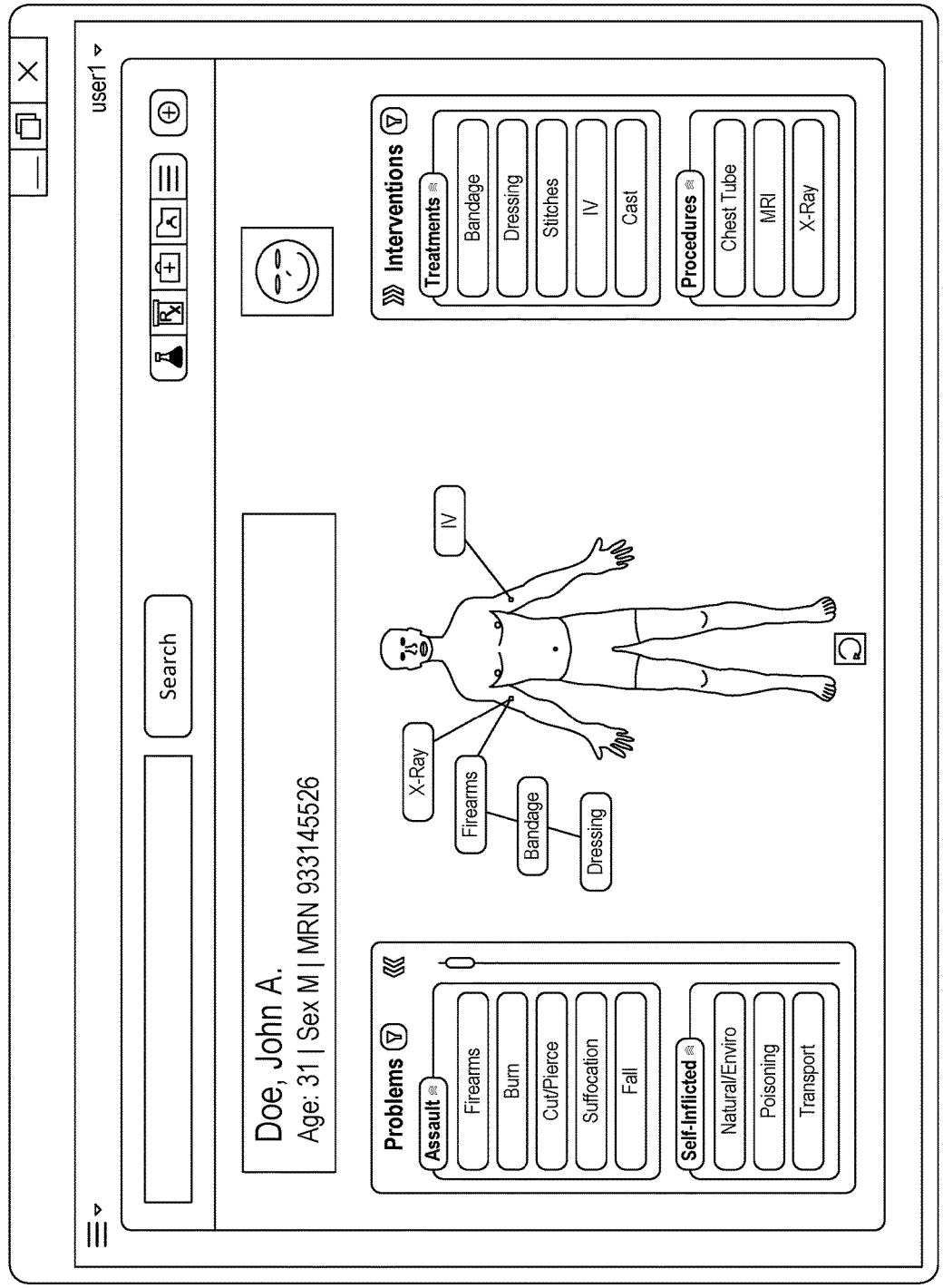

In accordance with one or more preferred implementations, association of additional items may effect automatic repositioning of displayed items associated with an avatar in order to accommodate legible display, as illustrated in FIG. 40.

Figure 41:
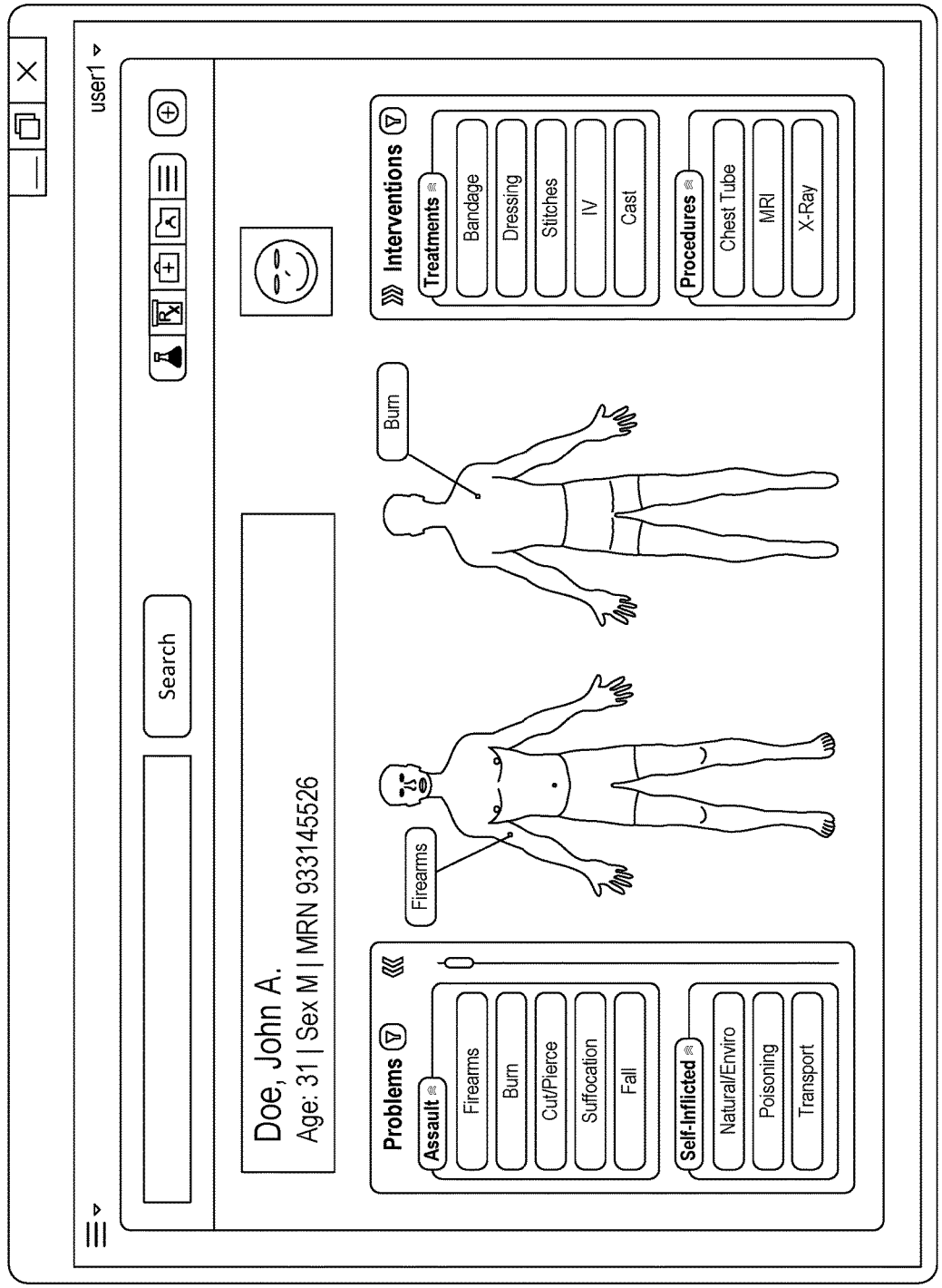

In accordance with one or more preferred implementations, an interface may include one or more user interface elements configured to allow a user to view an avatar from a different perspective, or rotate an avatar. In accordance with one or more preferred implementations, multiple views of an avatar may even be displayed at once, as illustrated in FIG. 41. In accordance with one or more preferred implementations, multiple views may only be displayed if one or more items are associated with each view.

In accordance with one or more preferred implementations, additional views or perspectives of an avatar may be utilized, and in accordance with one or more preferred implementations, a user may even be able to rotate a three dimensional avatar in one, two, or even three dimensions.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof

What is claimed is:

1. A processor-based method for operating a graphical user interface for a healthcare software application of an electronic device, comprising:
   (a) generating, via the electronic device, a first interface of the healthcare software application, the first interface comprising
      (i) an anatomical image avatar for a patient, the avatar comprising a plurality of hotspots associated with portions of the avatar,
      (ii) a first listing of a plurality of problems associated with at least one of the plurality of hotspot, and
      (iii) a second listing of a plurality of interventions associated with at least one of the plurality of problems associated with the at least one of the plurality of hotspots;
   (b) receiving, via one or more input devices associated with the electronic device, a first user input corresponding to dragging and dropping of a first listed problem item from the first listing of the plurality of problems over a first hotspot of the plurality of hotspots;
   (c) receiving, via the one or more input devices associated with the electronic device, a second user input corresponding to dragging and dropping of a first listed intervention item from the second listing of the plurality of interventions over the first hotspot; and
   (d) in response to the received first user input and the received second user input, modifying, via the electronic device, the first interface to display a detailed first interface portion, the displaying of the detailed first interface portion comprising:
      a visual indication of the first listed problem item,
      a visual indication of the first listed intervention item, and
      visual links connecting the visual indication of the first listed problem item and the visual indication of the first listed intervention item with the first hotspot on the anatomical image avatar.

2. The processor-based method of claim 1, further comprising generating an enlarged view of the hotspot when receiving user input corresponding to dragging and dropping of the first listed problem item.

3. The processor-based method of claim 2, further comprising generating an enlarged view of the hotspot when receiving user input corresponding to dragging and dropping of the first listed intervention item.

4. The processor-based method of claim 3, further comprising generating an enlarged view of the hotspot when receiving user input corresponding to dragging and dropping of a second listed intervention item.

5. The processor-based method of claim 1, further comprising expanding the first hotspot by generating a drill-down anatomical view when receiving user input corresponding to dragging and dropping of the first listed problem item.

6. The processor-based method of claim 5, further comprising expanding the first hotspot by generating a drill-down anatomical view when receiving user input corresponding to dragging and dropping of the first listed intervention item.

7. The processor-based method of claim 6, further comprising expanding the first hotspot by generating a drill-down anatomical view when receiving user input corresponding to dragging and dropping of a second listed intervention item.

8. The processor-based method of claim 1, further comprising receiving, via the one or more input devices associated with the electronic device, user input corresponding to dragging and dropping of one or more additional listed intervention items of the plurality of interventions over the first intervention item, and associating, via the electronic device the one or more additional listed intervention items with the first intervention item as a result thereof.

9. One or more non-transitory computer readable media containing computer-executable instructions for performing a method related to a graphical user interface for a healthcare software application, comprising:

(a) generating, via the electronic device, a first interface of the healthcare software application, the first interface comprising
  (i) an anatomical image avatar for a patient, the avatar comprising a plurality of hotspots associated with portions of the avatar,
  (ii) a first listing of a plurality of problems associated with at least one of the plurality of hotspot, and
  (iii) a second listing of a plurality of interventions that can be associated with at least one of the plurality of problems associated with the at least one of the plurality of hotspots;
(b) receiving, via one or more input devices associated with the electronic device, a first user input corresponding to dragging and dropping of a first listed problem item from the first listing of the plurality of problems over a first hotspot of the plurality of hotspots;
(c) receiving, via the one or more input devices associated with the electronic device, a second user input corresponding to dragging and dropping of a first listed intervention item from the second listing of the plurality of interventions over the first hotspot; and
(d) in response to the received first user input and the received second user input, modifying, via the electronic device, the first interface to display a detailed first interface portion, the displaying of the detailed first interface portion comprising:
  a visual indication of the first listed problem item,
  a visual indication of the first listed intervention item, and
  visual links connecting the visual indication of the first listed problem item and the visual indication of the first listed intervention item with the first hotspot on the anatomical image avatar.

10. The one or more non-transitory computer readable media of claim 9, further comprising generating an enlarged view of the hotspot when receiving user input corresponding to dragging and dropping of the first listed problem item.

11. The one or more non-transitory computer readable media of claim 10, further comprising generating an enlarged view of the hotspot when receiving user input corresponding to dragging and dropping of the first listed intervention item.

12. The one or more non-transitory computer readable media of claim 11, further comprising generating an enlarged view of the hotspot when receiving user input corresponding to dragging and dropping of a second listed intervention item.

13. The one or more non-transitory computer readable media of claim 9, further comprising expanding the first hotspot by generating a drill-down anatomical view when receiving user input corresponding to dragging and dropping of the first listed problem item.

14. The one or more non-transitory computer readable media of claim 13, further comprising expanding the first hotspot by generating a drill-down anatomical view when receiving user input corresponding to dragging and dropping of the first listed intervention item.

15. The one or more non-transitory computer readable media of claim 14, further comprising expanding the first hotspot by generating a drill-down anatomical view when receiving user input corresponding to dragging and dropping of a second listed intervention item.

16. The one or more non-transitory computer readable media of claim 9, further comprising receiving, via the one or more input devices associated with the electronic device, user input corresponding to dragging and dropping of one or more additional listed intervention items of the plurality of interventions over the first intervention item, and associating, via the electronic device the one or more additional listed intervention items with at least one of the first intervention items and second intervention items as a result thereof.

17. A processor-based method for operating a graphical user interface for a healthcare software application of an electronic device, comprising:
(a) generating, via the electronic device, a first interface of the healthcare software application, the first interface comprising
  (i) an anatomical image avatar for a patient, the avatar comprising a plurality of hotspots associated with portions of the avatar,
  (ii) a first listing of a plurality of problems associated with at least one of the plurality of hotspot, and
  (iii) a second listing of a plurality of interventions associated with at least one of the plurality of problems associated with the at least one of the plurality of hotspots;
(b) receiving, via one or more input devices associated with the electronic device, a first user input corresponding to dragging and dropping of a first listed problem item from the first listing of the plurality of problems over a first hotspot of the plurality of hotspots;
(c) expanding the first hotspot by generating a drill-down anatomical view when receiving user input corresponding to dragging and dropping of the first listed problem item;
(d) receiving, via the one or more input devices associated with the electronic device, a second user input corresponding to dragging and dropping of a first listed intervention item from the second listing of the plurality of interventions over the first hotspot; and
(e) in response to the received first user input and the received second user input, modifying, via the electronic device, the first interface to display a detailed first interface portion, the displaying of the detailed first interface portion comprising:
  a visual indication of visually associating the first listed problem item, and
  a visual indication of the first listed intervention item, and
  visual links connecting the visual indication of the first listed problem item and the visual indication of the first listed intervention item with the first hotspot on the anatomical image avatar.

\* \* \* \* \*